US007271190B2

(12) United States Patent
Miyoshi et al.

(10) Patent No.: US 7,271,190 B2
(45) Date of Patent: Sep. 18, 2007

(54) INDAZOLE COMPOUNDS AS β3 ADRENOCEPTOR AGONIST

(75) Inventors: Shiro Miyoshi, Fuji (JP); Kohei Ogawa, Mishima (JP)

(73) Assignee: Asahi Kasei Pharma Corporation, Tokyo (JP)

(*) Notice: Subject to any disclaimer, the term of this patent is extended or adjusted under 35 U.S.C. 154(b) by 110 days.

(21) Appl. No.: 10/493,601

(22) PCT Filed: Oct. 25, 2002

(86) PCT No.: PCT/JP02/11087

§ 371 (c)(1),
(2), (4) Date: Apr. 26, 2004

(87) PCT Pub. No.: WO03/035620

PCT Pub. Date: May 1, 2003

(65) Prior Publication Data

US 2005/0020602 A1    Jan. 27, 2005

(30) Foreign Application Priority Data

Oct. 25, 2001  (JP)  ............................. 2001-327467

(51) Int. Cl.
    A61K 31/415    (2006.01)
    C07D 231/56    (2006.01)
(52) U.S. Cl. ................. 514/403; 548/361.1; 548/362.5
(58) Field of Classification Search ................ 514/415; 548/469
    See application file for complete search history.

(56) References Cited

U.S. PATENT DOCUMENTS

| 4,378,361 | A | 3/1983 | Schromm et al. | |
| 5,767,133 | A * | 6/1998 | Dow et al. | 514/339 |
| 5,859,044 | A | 1/1999 | Dow et al. | |
| 6,037,362 | A | 3/2000 | Miyoshi et al. | |
| 6,172,099 | B1 | 1/2001 | Miyoshi et al. | |
| 6,495,701 | B1 | 12/2002 | Matsubara et al. | |
| 6,861,444 | B2 * | 3/2005 | Ikuta et al. | 514/415 |
| 2003/0040538 | A1 | 2/2003 | Miyoshi et al. | |
| 2003/0191174 | A1 | 10/2003 | Ikuta et al. | |
| 2004/0102437 | A1 | 5/2004 | Takami et al. | |
| 2004/0138286 | A1 | 7/2004 | Imazaki et al. | |

FOREIGN PATENT DOCUMENTS

| DE | 24 29 253 | 6/1974 |
| DE | 26 51 572 C2 | 6/1977 |
| EP | 0 008 653 | 3/1980 |
| EP | 0 023 385 | 2/1981 |
| EP | 0 171 702 | 2/1986 |
| EP | 0 455 006 | 4/1991 |
| EP | 659 737 A2 | 6/1995 |
| EP | 1 174 425 A1 | 3/2000 |
| GB | 1 565 080 | 11/1976 |
| JP | 55-53262 | 4/1980 |
| JP | 58-41860 | 3/1983 |
| JP | 8-165276 | 6/1996 |
| WO | WO94/29290 | 12/1994 |
| WO | WO95/29159 | 11/1995 |
| WO | WO96/35670 | 11/1996 |
| WO | WO97/25311 | 7/1997 |
| WO | WO9901431 | 1/1999 |
| WO | WO 00/35890 | 6/2000 |
| WO | WO 00/59287 | 10/2000 |
| WO | WO 00/59885 | 10/2000 |
| WO | WO 01/56988 A1 | 8/2001 |
| WO | WO 01/83451 | 11/2001 |
| WO | WO 01/83452 | 11/2001 |
| WO | WO 01/83453 | 11/2001 |
| WO | WO 02/100833 A1 | 12/2002 |

OTHER PUBLICATIONS

Arch et al., "Atypical B-adrenoceptor on brown adipocytes as target for anti-obesity drugs", Nature, vol. 309, May 1984, pp. 163-165.
Arch et al., "Prospects for $B_3$-adrenoceptor agonists in the treatment of obesity and diabetes", international Journal of Obesity, 1996, vol. 20, pp. 191-199.
Largis et al., "Antidiabetic and Antiobesity Effects of a Highly Selective $B_3$-Adrenoceptor Agonist (CL 316,243)", Drug Development Research, 1994, vol. 32, pp. 69-76.
Fisher et al., "A Selective Human $B_3$ Adrenergic Receptor Agonist Increases Metabolic Rate in Rhesus Monkeys", J. Clin. Invest., 1998, vol. 101, pp. 2387-2393.
Fujimura et al., "Expression and Possible Functional Role of the B3-Adrenoceptor in Human and Rat Detrusor Muscle", The Journal of Urology, 1999, vol. 161, pp. 680-685.
Takeda et al., "Evidence for $B_3$-Adrenoceptor Subtypes in Relaxation of the Human Urinary Bladder Detrusor: Analysis by Molecular Biological and Pharmacological Methods", The Journal of Pharmacology and Experimental Therapeutics, 1999, vol. 288, pp. 1367-1373.
Cantello et al., "BRL 35135", Drugs of the Future, 1991, vol. 16, pp. 797-800.
Humber et al., "Disodium . . . A Potent B-Adreneric Agonist Virtually Specific for $B_3$ Receptors. A Promising Antidiabetic and Antiobesity Agent", J. Med. Chem, 1992, vol. 35, pp. 3081-3084.

* cited by examiner

Primary Examiner—Kamal A. Saeed
Assistant Examiner—Susannah L. Chung
(74) Attorney, Agent, or Firm—Young & Thompson

(57) ABSTRACT

A compound represented by the general formula I: I wherein R1 represents hydrogen, etc. $R^2$ represents $NHSO_2R^3$, etc., provided that $R^3$ represents $C_{1-6}$ alkyl, etc. $R^5$ represents hydrogen, etc. $R^6$ and $R^7$ may be the same or different and each independently represents hydrogen, etc. X represents oxygen, etc. Y represents oxygen, etc. $Z^1$ to $Z^6$ each represents carbon, etc. n is an integer of 0 to 6 and ast1 indicates that the carbon atom is asymmetric, and *2, in the case where $R^5$ is not hydrogen, indicates that the carbon atom is asymmetric or a salt of the compound.

10 Claims, No Drawings

INDAZOLE COMPOUNDS AS β3 ADRENOCEPTOR AGONIST

FIELD OF THE INVENTION

This invention relates to novel compounds which are useful as a medicine for treating and preventing diabetes, obesity, hyperlipidemia, digestive diseases, depression, fatty liver or urinary incontinence.

BACKGROUND OF THE INVENTION

Beta-adrenoreceptors were classified into three classes, β1-adrenoreceptor, β2-adrenoreceptor and β3-adrenoreceptor, and it was recognized that stimulation of β1 induces an increase in the heart rate and stimulation of β2 induces a relaxation of the smooth muscle tissue, thereby resulting in lowering the blood pressure. It was also recognized that stimulation of β3 facilitates the lipolysis in adipocytes, thereby resulting in increasing thermogenesis. Therefore, compounds having β3-agonist activity were shown to be useful as a medicine for treating and preventing diabetes, obesity and hyperlipidemia (*Nature*, vol. 309, pp. 163-165, 1984; *Int. J. Obes. Relat. Metab. Disord.*, vol. 20, pp. 191-199, 1996; *Drug Development Research*, vol. 32, pp. 69-76, 1994; *J. Clin. Invest.*, vol. 101, pp. 2387-2393, 1998). Recently, it was shown that p3-adrenoreceptor is expressed in the detrusor and a β3-agonist induces a relaxation of the detrusor (*J. Urinol.*, vol. 161, pp. 680-685, 1999; *J. Pharmacol. Exp. Ther.*, vol. 288, pp. 1367-1373, 1999). Therefore, compounds having β3-agonist activity are expected to be useful as a medicine for treating and preventing urinary incontinence.

Some compounds showing a β3-agonist activity have been known. Compounds having high selectivity or having low β1- and β2-stimulating activities are particularly required when their usefulness as a medicine is taken into consideration. This is because compounds having both β1- and β2-stimulating activities induce side effects such as increase in the heart rate and lowering of the blood pressure, as set forth above.

So far, the following compounds have been exemplified as compounds relating to β3:

the compound (BRL 37344) having the following structural formula described in EP 023385 and the literature (*Drugs of the future*, vol. 16, p. 797 (1991)):

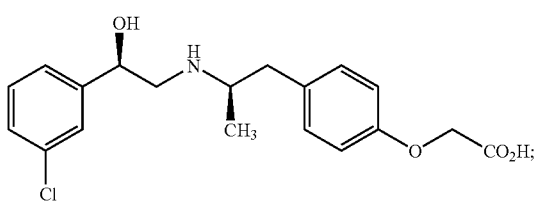

the compound (CL 316,243) having the following structural formula described in EP 0455006 and the literature (*J. Med. Chem.*, vol. 35, p. 3081 (1992)):

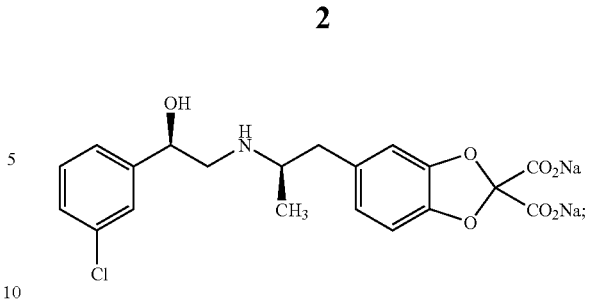

and the compound having the following structural formula described in WO 94/29290:

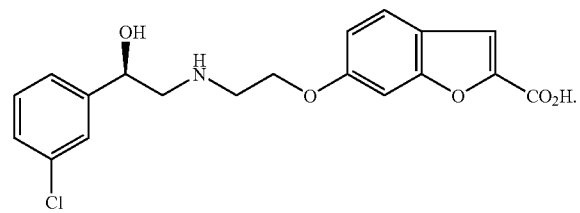

Further, EP 0659737 discloses a variety of compounds and specifically describes as an example in Example 1 in the text of specification the compound having the following structural formula:

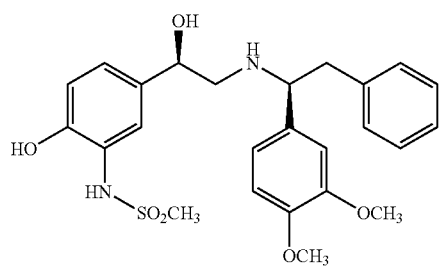

However, the chemical structures of the above compounds are clearly distinct from those of the claimed compounds of the present invention.

In addition, the compound described in EP 171702 and having the following structural formula:

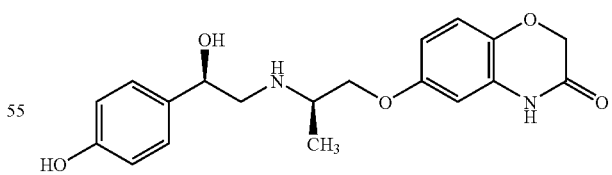

has been known as having heart rate-increasing activity, myocardial contraction enhancement and antiobestic activity. However, this compound acts on the heart and is different from the compound of the present invention in terms of its chemical structure and in that the former strongly acts on the heart.

Further, the compound described in JP-A-55-53262 and JP-A-58-41860 and having the following structural formula:

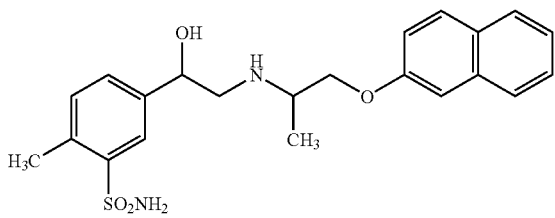

is known as having α, β-blocking activity, namely the effect of lowering blood pressure; and the compound described in DE 2651572 and having the following structural formula:

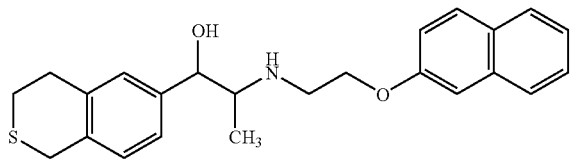

is known as having vasodilator action. However, these compounds are different from the compounds of the present invention in terms of their chemical structures and intended uses.

The present inventors formerly invented compounds having excellent β3-agonist activity and disclosed compounds represented by, for example, the following structural formula in WO 97/25311.

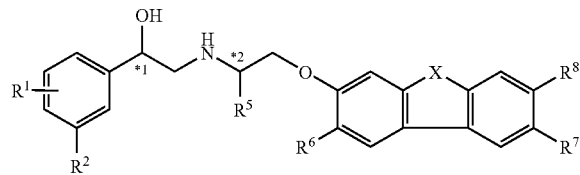

The above compounds, however, are different from the compounds of the present invention in their chemical structures.

Further, the present inventors disclosed compounds represented by, for example, the following structural formula in WO 01/83451.

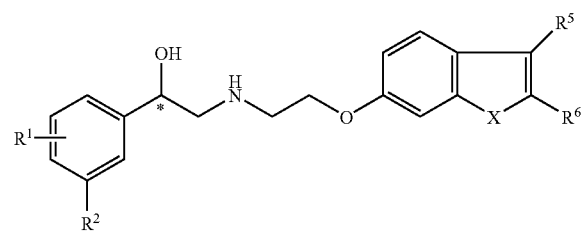

DISCLOSURE OF THE INVENTION

There has been a need for a novel and useful β3-selective agonist which can be used for treating and preventing diabetes, obesity, hyperlipidemia, urinary incontinence and the like.

In order to solve the above problems, the present inventors synthesized a variety of compounds and studied their activities. As a result, the inventions disclosed in the above-mentioned WO 01/83451 were completed. It was thought, however, that there was a need to provide further useful compounds. The present inventors have earnestly studied and synthesized many more compounds. As a result, the present inventors have found that a novel bicyclic compound of the general formula (I) set forth below, has selective β3-agonist activity and that it can exhibit sufficient hypoglycemic and lipolytic activities with high safety and further has anti-urinary incontinence activity due to a relaxation of the detrusor, completes the present invention.

That is, the present invention includes the following inventions.

(1) A compound of the general formula (I):

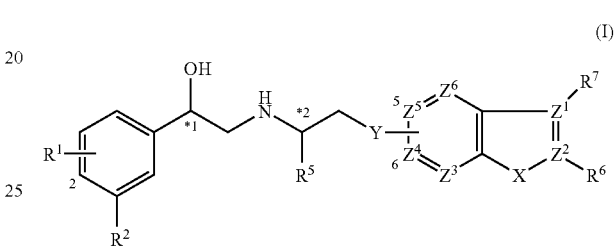

or a salt thereof, wherein $R^1$ represents a hydrogen atom, a hydroxyl group or a halogen atom;

$R^2$ represents $NHSO_2R^3$ or $SO_2NR\ R$;

$R^3$ represents a $(C_1-C_6)$alkyl group, a benzyl group, a phenyl group or $NR^4R^{4'}$;

$R^4$ and $R^{4'}$ may be the same or different and each independently represents a hydrogen atom or a $(C_1-C_6)$alkyl group;

$R^5$ represents a hydrogen atom or a $(C_1-C_6)$alkyl group;

$R^6$ and $R^7$ may be the same or different and each independently represents a hydrogen atom, a $(C_1-C_6)$alkyl group, a $(C_1-C_6)$alkyl group optionally substituted with one or more halogen atoms, an optionally substituted $-(CH_2)_n$-phenyl group, $-CH=CH-CO_2R^5$ or $-(CH_2)_n-R^8$;

$R^8$ represents $OR^5$, CN, $NR^{41}R^{41'}$, $CO_2R^5$, $SO_3R^5$, $SO_2(C_1-C_6)$ alkyl, $SO_2NR^{41}R^{41'}$, $C(=O)R^5$, $C(=O)NR^{41}R^{41'}$ or $NR^{51}COR^5$, wherein $R^5$ is as defined above; $R^{51}$ represents a hydrogen atom or a $(C_1-C_6)$alkyl group; $R^{41}$ and $R^{41'}$ may be the same or different and each independently represents a hydrogen atom, a $(C_1-C_6)$alkyl group or a $(C_3-C_6)$cycloalkyl group, or $R^{41}$ and $R^{41'}$ taken together represent a $(C_2-C_6)$alkylene group; or $R^8$ is a heterocycle selected from pyridyl, pyrimidinyl, pyrazinyl, thiazolyl, oxazolyl, imidazolyl, triazolyl, 1,2,4-oxadiazolyl, isoxazolyl, tetrazolyl, pyrazolyl, hexamethyleneiminyl, piperidinyl and pyrrolidinyl, wherein one of the ring nitrogen atoms of imidazolyl, triazolyl and tetrazolyl may be optionally substituted with a $(C_1-C_6)$alkyl group which is optionally substituted with one or more halogen atoms; wherein with respect to one or more of the ring carbon atoms of the each heterocycle, each of them may be optionally substituted with one or more substituents which are independently selected from hydrogen, a $(C_1-C_6)$alkyl group optionally substituted with one or more halogen atoms, a halogen atom, nitro, cyano and $-(CH_2)_n-R^9$; and wherein the ring nitrogen atom of hexamethyleneiminyl, piperidinyl and pyrrolidinyl may be substituted with a ($C_1$-$C_6$)alkyl group, a ($C_3$-$C_6$)cycloalkyl group, $COR^5$, $COOR^5$, $CONR^4R^{4'}$ or $SO_2R^5$;

$R^9$ represents $NR^4R^{4'}$, $CO_2R^5$, $C(=O)$—$NR^4R^{4'}$, $OR^5$, $SO_3R^5$, $SO_2(C_1$-$C_6)$ alkyl or $SO_2NR^4R^{4'}$, wherein $R^5$, $R^4$ and $R^{4'}$ are as defined above; provided that the combinations of $R^6$ and $R^7$ are excluded in which $R^6$ and $R^7$ are the same or different and are each selected from a hydrogen atom, ($C_1$-$C_6$)alkyl and an optionally substituted —$(CH_2)_m$-phenyl group wherein m is 0 or 1;

X represents $NR^{10}$, an oxygen atom or a sulfur atom;

Y represents an oxygen atom, NH, a sulfur atom or a methylene group;

all of $Z^1$ to $Z^6$ represent a carbon atom; or one of them represents a nitrogen atom and the others represent a carbon atom;

provided that when $Z^1$ is a nitrogen atom, then $R^7$ is absent; when $Z^2$ is a nitrogen atom, then $R^6$ is absent; and when any one of $Z^3$ to $Z^6$ is a nitrogen atom, then no linkage is generated between Y and the corresponding Z;

$R^{10}$ represents a hydrogen atom, an optionally substituted —$(CH_2)_n$—phenyl group, a —($C_1$-$C_{10}$)alkyl group or —$(CH_2)_n$—$R^8$, wherein $R^8$ is as defined above;

n is an integer of 0 to 6;

*1 represents an asymmetric carbon atom; and

*2 represents an asymmetric carbon atom when $R^5$ is other than a hydrogen atom.

(2) A compound as defined in the above (1) having the general formula (I), wherein $Z^1$ is a nitrogen atom or a carbon atom; and each of $Z^2$ to $Z^6$ is a carbon atom, or a salt thereof.

(3) A compound as defined in the above (1) or (2) having the general formula (I), wherein $R^8$ is $OR^5$, CN, $NR^{41}R^{41'}$, $CO_2R^5$, $SO_3R^5$, $SO_2(C_1$-$C_6)$alkyl, $SO_2NR^{41}R^{41'}$, $C(=O)R^5$ or $C(=O)NR^{41}R^{41'}$, wherein $R^5$ is as defined above; and $R^{41}$ and $R^{41'}$ may be the same or different and are each independently a hydrogen atom or a ($C_1$-$C_6$)alkyl group, or $R^{41}$ and $R^{41'}$ taken together represent a ($C_2$-$C_6$)alkylene group; or $R^8$ is a heterocycle selected from pyridyl, pyrimidinyl, pyrazinyl, thiazolyl, oxazolyl, imidazolyl, triazolyl, 1,2,4-oxadiazolyl, isoxazolyl, tetrazolyl and pyrazolyl, wherein one of the ring nitrogen atoms of imidazolyl, triazolyl and tetrazolyl may be optionally substituted with a ($C_1$-$C_6$)alkyl group which is optionally substituted with one or more halogen atoms; wherein with respect to one or more of the ring carbon atoms of the each heterocycle, each of them may be optionally substituted with one or more substituents which are independently selected from hydrogen, a ($C_1$-$C_6$) alkyl group optionally substituted with one or more halogen atoms, a halogen atom, nitro, cyano and —$(CH_2)_n$—$R^9$, wherein $R^9$ is as defined above, or a salt thereof.

(4) A compound as defined in the above (1) having the general formula (I), wherein $Z^2$ is a nitrogen atom; $R^6$ is absent; and each of $Z^1$ and $Z^3$ to $Z^6$ is a carbon atom, or a salt thereof.

(5) A compound as defined in any one of the above (1) to (4) having the general formula (I), wherein $R^1$ is present on para position (2-position) with respect to the amino alcohol side chain, or a salt thereof.

(6) A compound as defined in any one of the above (1) to (5) having the general formula (I), wherein Y is an oxygen atom, NH or a sulfur atom, or a salt thereof.

(7) A compound as defined in any one of the above (1) to (6) having the general formula (I), wherein X is NH, an oxygen atom or a sulfur atom, or a salt thereof.

(8) A compound as defined in any one of the above (1), (2) and (4), which is a compound selected from the group consisting of:

ethyl (R)-6-[2-[2-(3-methylsulfonylamino)phenyl-2-hydroxyethylamino]ethoxy]-3-methyl-1H-indole-2-carboxylate;

(R)-6-[2-[2-(3-methylsulfonylamino)phenyl-2-hydroxyethylamino]ethoxy]-3-methyl-1H-indole-2-carboxylic acid;

ethyl (R)-6-[2-[2-(3-methylsulfonylamino)phenyl-2-hydroxyethylamino]ethoxy]-2-methyl-1H-indole-3-carboxylate;

(R)-6-[2-[2-(3-methylsulfonylamino)phenyl-2-hydroxyethylamino]ethoxy]-2-methyl-1H-indole-3-carboxylic acid;

(R)-N-[3-[2-[2-(3-hydroxymethyl-2-methyl-1H-indol-6-yloxy)ethylamino]-1-hydroxyethyl]phenyl]methanesulfonamide;

(R)-N-[3-[2-[2-[3-(N',N'-dimethylamino)methyl-2-methyl-1H-indol-6-yloxy]ethylamino]-1-hydroxyethyl]phenyl]methanesulfonamide;

ethyl (R)-[6-[2-[2-(3-methylsulfonylamino)phenyl-2-hydroxyethylamino]ethoxy]-2-methyl-1H-indol-3-yl]acetate;

(R)-[6-[2-[2-(3-methylsulfonylamino)phenyl-2-hydroxyethylamino]ethoxy]-2-methyl-1H-indol-3-yl]acetic acid;

ethyl (R)-3-[6-[2-[2-(3-methylsulfonylamino)phenyl-2-hydroxyethylamino]ethoxy]-2-methyl-1H-indol-3-yl]acrylate;

(R)-3-[6-[2-[2-(3-methylsulfonylamino)phenyl-2-hydroxyethylamino]ethoxy]-2-methyl-1H-indol-3-yl]acrylic acid;

ethyl (R)-3-[6-[2-[2-(3-methylsulfonylamino)phenyl-2-hydroxyethylamino]ethoxy]-2-methyl-1H-indol-3-yl]propionate;

(R)-3-[6-[2-[2-(3-methanesulfonylamino)phenyl-2-hydroxyethylamino]ethoxy]-2-methyl-1H-indol-3-yl]propionic acid;

(R)-N-[3-[2-[2-[3-(2-aminoethyl)-2-methyl-1H-indol-6-yloxy]ethyl amino]-1-hydroxyethyl]phenyl]methanesulfonamide;

(R)-N-[3-[2-[2-[3-(2-N',N'-dimethylamino)ethyl-2-methyl-1H-indol-6-yloxy]ethylamino]-1-hydroxyethyl]phenyl]methanesulfonamide;

(R)-N-[3-[2-[2-[3-acetyl-2-methyl-1H-indol-6-yloxy]ethylamino]-1-hydroxyethyl]phenyl]methanesulfonamide;

ethyl (R)-[6-[2-[2-(3-methylsulfonylamino)phenyl-2-hydroxyethylamino]ethoxy]-2-ethyl-1H-indol-3-yl]acetate;

(R)-[6-[2-[2-(3-methylsulfonylamino)phenyl-2-hydroxyethylamino]ethoxy]-2-ethyl-1H-indol-3-yl]acetic acid;

ethyl (R)-[6-[2-[2-(3-methanesulfonylamino)phenyl-2-hydroxyethylamino]ethoxy]-2-phenyl-1H-indol-3-yl]acetate;

(R)-[6-[2-[2-(3-methylsulfonylamino)phenyl-2-hydroxyethylamino]ethoxy]-2-phenyl-1H-indol-3-yl]acetic acid;

ethyl (R)-[6-[2-[2-(4-chloro-3-methylsulfonylamino)phenyl-2-hydroxyethylamino]ethoxy]-2-methyl-1H-indol-3-yl] acetate;

(R)-[6-[2-[2-(4-chloro-3-methylsulfonylamino)phenyl-2-hydroxyethylamino]ethoxy]-2-methyl-1H-indol-3-yl] acetic acid;

ethyl (R)-[6-[2-[2-(4-fluoro-3-methylsulfonylamino)phenyl-2-hydroxyethyl amino]ethoxy]-2-methyl-1H-indol-3-yl]acetate;

(R)-[6-[2-[2-(4-fluoro-3-methylsulfonylamino)phenyl-2-hydroxyethylamino]ethoxy]-2-methyl-1H-indol-3-yl]acetic acid;

(R)-[6-[2-[2-(4-hydroxy-3-methylsulfamoyl)phenyl-2-hydroxyethylamino]ethoxy]-2-methyl-1H-indol-3-yl] acetic acid;

(R)-[6-[2-[2-(3-methylsulfonylamino)phenyl-2-hydroxyethylamino]ethoxy]-2-(2-methoxyethyl)-1H-indol-3-yl]acetic acid;

(R)-3-[6-[2-[2-(3-methylsulfonylamino)phenyl-2-hydroxyethylamino]ethoxy]-2-(2-methoxyethyl)-1H-indol-3-yl]propionic acid;

(R)-N-[3-[2-[2-[2-(2-methoxyethyl)-3-methyl-1H-indol-6-yloxy]ethylamino]-1-hydroxyethyl]phenyl]methanesulfonamide;

(R)-N-[3-[2-[2-[3-ethyl-2-(2-methoxyethyl)-1H-indol-6-yloxy]ethylamino]-1-hydroxyethyl]phenyl]methanesulfonamide;

ethyl (R)-6-[2-[2-(3-methylsulfonylamino)phenyl-2-hydroxyethylamino]ethylamino]-3-methyl-1H-indole-2-carboxylate;

(R)-6-[2-[2-(3-methylsulfonylamino)phenyl-2-hydroxyethylamino]ethylamino]-3-methyl-1H-indole-2-carboxylic acid;

ethyl (R)-[6-[2-[2-(4-chloro-3-methylsulfonylamino)phenyl-2-hydroxyethylamino]ethoxy]-3-methyl-1H-indol-2-yl]acetate;

ethyl (R)-[6-[2-[2-(4-fluoro-3-methylsulfonylamino)phenyl-2-hydroxyethylamino]ethoxy]-3-methyl-1H-indol-2-yl]acetate;

ethyl (R,R)-6-[2-[2-(4-fluoro-3-methylsulfonylamino)phenyl-2-hydroxyethylamino]propoxy]-3-methyl-1H-indole-2-carboxylate;

ethyl (R)-6-[2-[2-(3-methylsulfonylamino)phenyl-2-hydroxyethylamino]ethoxy]-3-methyl-benzofuran-2-carboxylate;

(R)-6-[2-[2-(3-methylsulfonylamino)phenyl-2-hydroxyethylamino]ethoxy]-3-methyl-benzofuran-2-carboxylic acid;

ethyl (R)-[6-[2-[2-(3-methylsulfonylamino)phenyl-2-hydroxyethylamino]ethoxy]-2-methyl-benzofuran-3-yl]acetate;

(R)-[6-[2-[2-(3-methylsulfonylamino)phenyl-2-hydroxyethylamino]ethoxy]-2-methyl-benzofuran-3-yl]acetic acid;

ethyl (R)-[6-[2-[2-(3-methylsulfonylamino)phenyl-2-hydroxyethylamino]ethoxy]-2-phenylbenzothiophen-3-yl]acetate;

ethyl (R)-3-[6-[2-[2-(3-methylsulfonylamino)phenyl-2-hydroxyethylamino]ethoxy]-2-phenylbenzothiophen-3-yl]propionate;

(R)-N-[3-[2-[2-(2-pyrrolidylcarbonylbenzofuran-6-yloxy)ethylamino]-1-hydroxyethyl]phenyl]methanesulfonamide;

(R)-N-[3-[2-[2-[2-(isoxazol-3-yl)benzofuran-6-yloxy]ethylamino]-1-hydroxyethyl]phenyl]methanesulfonamide;

ethyl (R)-5-[2-[2-(3-methylsulfonylamino)phenyl-2-hydroxyethylamino]ethoxy]-3-methyl-1H-indole-2-carboxylate;

(R)-1-benzyl-6-[2-[2-(3-methylsulfonylamino)phenyl-2-hydroxyethylamino]ethoxy]-1H-indole-2-carboxylic acid;

(R)-1-[3-(N'-methylsulfonylamino)phenyl]methyl-6-[2-[2-(3-methylsulfonylamino)phenyl-2-hydroxyethylamino]ethoxy]-1H-indole-2-carboxylic acid;

(R)-1-[4-(N'-methylsulfonylamino)phenyl]methyl-6-[2-[2-(3-methylsulfonylamino)phenyl-2-hydroxyethylamino]ethoxy]-1H-indole-2-carboxylic acid;

(R)-N-[3-[2-[2-(2,3-ditrifluoromethyl-1H-indol-6-yloxy)ethylamino]-1-hydroxyethyl]phenyl]methanesulfonamide;

(R)-N-[3-[1-hydroxy-2-[2-(3-methyl-2-pyridin-3-yl-1H-indol-6-yloxy)ethylamino]ethyl]phenyl]methanesulfonamide;

(R)-N-[3-[2-[2-(3-ethyl-2-pyridin-3-yl-1H-indol-6-yloxy)ethylamino]-1-hydroxyethyl]phenyl]methanesulfonamide;

(R)-N-[3-[1-hydroxy-2-[2-(3-methyl-2-pyridin-4-yl-1H-indol-6-yloxy)ethylamino]ethyl]phenyl]methanesulfonamide;

(R)-N-[3-[2-[2-[2-(N'-t-butyloxycarbonylpiperidin-3-yl)-3-methyl-1H-indol-6-yloxy]ethylamino]-1-hydroxyethyl]phenyl]methanesulfonamide;

(R)-N-[3-[2-[1-hydroxy-2-(3-methyl-2-piperidin-3-yl-1H-indol-6-yloxy)ethylamino]ethyl]phenyl]methanesulfonamide;

(R)-N-[3-[2-[2-[3-(2-acetylaminoethyl)-2-methyl-1H-indol-6-yloxy]ethylamino]-1-hydroxyethyl]phenyl]methanesulfonamide;

ethyl (R)-3-[6-[2-[2-hydroxy-2-(3-methylsulfonylaminophenyl)ethylamino]ethoxy]-3-phenyl-1H-indol-2-yl]propionate;

(R)-N-[2-fluoro-5-[1-hydroxy-2-[2-(3-methyl-2-pyridin-3-yl-1H-indol-6-yloxy)ethylamino]ethyl]phenyl]methanesulfonamide;

ethyl (R)-3-[6-[2-[2-(4-fluoro-3-methylsulfonylaminophenyl)-2-hydroxyethylamino]ethoxy]-3-methyl-1H-indol-2-yl]propionate;

(R)-3-[3-methyl-6-[2-[2-(3-methylsulfonylaminophenyl)-2-hydroxyethyl]amino]ethoxy]-1H-indol-2-yl]-N,N-dimethylpropionamide;

ethyl (R)-3-[3-methyl-6-[2-[2-(3-methylsulfonylaminophenyl)-2-hydroxyethylamino]ethoxy]-1H-indol-2-yl]propionate;

ethyl (R)-2-[3-methyl-6-[2-[2-(3-methylsulfonylaminophenyl)-2-hydroxyethylamino]ethoxy]-1H-indol-2-yl]acetate;

(R)-N-[3-[2-[2-(3-methylindazol-6-yloxy)ethylamino]-1-hydroxyethyl]phenyl]methanesulfonamide;

(R)-N-[3-[2-[2-(1-benzyl-3-methylindazol-6-yloxy)ethylamino]-1-hydroxyethyl]phenyl]methanesulfonamide;

(R)-N-[3-[2-[2-(3-methoxyindazol-6-yloxy)ethylamino]-1-hydroxyethyl]phenyl]methanesulfonamide;

(R)-N-[5-[2-[2-(3-methylindazol-6-yloxy)ethylamino]-1-hydroxyethyl]-2-fluorophenyl]methanesulfonamide;

(R)-N-[5-[2-[2-(3-methylindazol-6-yloxy)ethylamino]-1-hydroxyethyl]-2-chlorophenyl]methanesulfonamide;

(R)-N-methyl-[5-[2-[2-(3-methylindazol-6-yloxy)ethylamino]-1-hydroxyethyl]-2-hydroxyl]benzenesulfonamide; and (R,R)-N-[3-[1-hydroxy-2-[1-methyl-2-(3-methylindazol-6-yloxy]ethylamino]ethyl]phenyl]methanesulfonamide, or a salt thereof.

(9) A medicine comprising a compound defined in the above (1) or a salt thereof as an active ingredient.

(10) A medicine as defined in the above (9), wherein the medicine is for treating or preventing any one of diabetes, obesity, hyperlipidemia and urinary incontinence.

Unless otherwise specified, "halogen atom" as used herein means a fluorine atom, a chorine atom, a bromine atom or an iodine atom. In addition, "$(C_1-C_6)$alkyl group" means a straight or branched saturated hydrocarbon group containing from 1 to 6 carbon atoms and specifically means methyl, ethyl, n-propyl, i-propyl, n-butyl, i-butyl, sec-butyl, tert-butyl, n-pentyl, i-pentyl, neopentyl, n-hexyl or the like. "$(C_3-C_6)$cycloalkyl group" means a cyclic saturated hydrocarbon group containing from 3 to 6 carbon atoms and specifically means cyclopropyl, cyclobutyl, cyclopentyl, cyclohexyl, or the like.

$R^1$ represents a hydrogen atom, a hydroxyl group or a halogen atom. Examples thereof include a hydrogen atom, a hydroxyl group, a fluorine atom, a chlorine atom, a bromine atom and an iodine atom. Preferred examples thereof include a hydrogen atom, a hydroxyl group, a fluorine atom, a chlorine atom and a bromine atom. Although the position on the benzene ring at which $R^1$ is attached is not limited, the position is preferably ortho- or para-position with respect to the aminoethanol side-chain, with para-position (2-position) being particularly preferred.

$R^2$ represents $NHSO_2R^3$ or $SO_2NR^4R^{4'}$, wherein $R^3$ represents an alkyl group containing from 1 to 6 carbon atoms, a benzyl group, a phenyl group or $NR^4R^{4'}$ and wherein $R^4$ and $R^{4'}$ may be the same or different and each independently represents a hydrogen atom or an alkyl group containing from 1 to 6 carbon atoms. Among the above, specific examples of $R^2$ include $NHSO_2CH_3$, $NHSO_2C_2H_5$, $NHSO_2C_6H_5$, $NHSO_2CH_2C_6H_5$, $SO_2NHCH_3$, $SO_2NHC_2H_5$, $NHSO_2N(CH_3)_2$ and $NHSO_2N(C_2H_5)_2$. Particularly preferred examples include $NHSO_2CH_3$, $SO_2NHCH_3$ and $NHSO_2N(CH_3)_2$.

Within the combinations of $R^1$ and $R^2$, the combination in which $R^1$ is a hydrogen, fluorine, chlorine or bromine atom at para-position (2-position) and $R^2$ is $NHSO_2CH_3$ or $NHSO_2N(CH_3)_2$ is preferred. The combination in which $R^1$ is a hydroxyl group at para-position (2-position) and $R^2$ is $SO_2NHCH_3$ is also preferred.

$R^5$ and $R^{51}$ are a hydrogen atom or a $(C_1-C_6)$alkyl group. Examples thereof include a hydrogen atom, methyl, ethyl, n-propyl, i-propyl, n-butyl, i-butyl, sec-butyl, tert-butyl, n-pentyl, i-pentyl, neopentyl and n-hexyl, with a hydrogen atom, methyl or ethyl being preferred.

All of $Z^1$ to $Z^6$ represent a carbon atom; or one of them represents a nitrogen atom and the others represent a carbon atom. For example, the meanings of $Z^1$ to $Z^6$ include the case in which all of them represent a carbon atom, the case in which $Z^1$ represents a nitrogen atom and $Z^2$ to $Z^6$ represent a carbon atom, the case in which $Z^2$ represents a nitrogen atom and $Z^1$ and $Z^3$ to $Z^6$ represent a carbon atom, and the case in which $Z^3$ represents a nitrogen atom and $Z^1$, $Z^2$ and $Z^4$ to $Z^6$ represent a carbon atom. Preferred examples of the meanings of $Z^1$ to $Z^6$ include the case in which all of them represent a carbon atom, the case in which $Z^1$ represents a nitrogen atom and $Z^2$ to $Z^6$ represent a carbon atom, and the case in which $Z^2$ represents a nitrogen atom and $Z^1$ and $Z^3$ to $Z^6$ represent a carbon atom.

$R^6$ and $R^7$ may be the same or different and each independently represents a hydrogen atom, a $(C_1-C_6)$alkyl group, a $(C_1-C_6)$alkyl group optionally substituted with one or more halogen atoms, an optionally substituted $—(CH_2)_n$-phenyl group, $—CH=CH—CO_2R^5$ or $—(CH_2)_n—R^8$. $R^8$ represents $OR^5$, $CN$, $NR^{41}R^{41'}$, $CO_2R^5$, $SO_2(C_1-C_6)$alkyl, $SO_2NR^{41}R^{41'}$, $C(=O)R^5$, $C(=O)NR^{41}R^{41'}$ or $NR^{51}COR^5$, wherein $R^5$ and $R^{51}$ are as defined above and wherein $R^{41}$ and $R^{41'}$ may be the same or different and each independently represents a hydrogen atom, a $(C_1-C_6)$alkyl group or a $(C_3-C_6)$cycloalkyl group, or $R^{41}$ and $R^{41'}$ taken together represent a $(C_2-C_6)$alkylene group; or $R^8$ is a heterocycle selected from pyridyl, pyrimidinyl, pyrazinyl, thiazolyl, oxazolyl, imidazolyl, triazolyl, 1,2,4-oxadiazolyl, isoxazolyl, tetrazolyl, pyrazolyl, hexamethyleneiminyl, piperidinyl and pyrrolidinyl, wherein one of the ring nitrogen atoms of imidazolyl, triazolyl and tetrazolyl may be optionally substituted with a $(C_1-C_6)$alkyl group which is optionally substituted with one or more halogen atoms; wherein with respect to one or more of the ring carbon atoms of the each heterocycle, each of them may be optionally substituted with one or more substituents which are independently selected from hydrogen, a $(C_1-C_6)$alkyl group optionally substituted with one or more halogen atoms, a halogen atom, nitro, cyano and $—(CH_2)_n—R^9$; and wherein the ring nitrogen atom of hexamethyleneiminyl, piperidinyl and pyrrolidinyl may be substituted with a $(C_1-C_6)$alkyl group, a $(C_3-C_6)$ cycloalkyl group, $COR^5$, $COOR^5$, $CONR^4R^{4'}$ or $SO_2R^5$. $R^9$ represents $NR^4R^{4'}$, $CO_2R^5$, $C(=O)—NR^4R^{4'}$, $OR^5$, $SO_3R^5$, $SO_2(C_1-C_6)$alkyl or $SO_2NR^4R^{4'}$, wherein $R^5$, $R^4$ and $R^{4'}$ are as defined above.

$R^6$ and $R^7$ are as defined above, provided that the combinations of $R^6$ and $R^7$ are excluded in which they are each independently selected from a hydrogen atom, an alkyl group containing from 1 to 6 carbon atoms and an optionally substituted $—(CH_2)_n$-phenyl group wherein n=0 or 1. With respect to the combinations of $R^6$ and $R^7$, preference is given to the combination in which $R^6$ is any one of 3-pyridyl, 4-pyridyl, 3-piperidinyl, N-t-butyloxycarbonyl-3-piperidinyl, 2-ethoxycarbonylethyl, 2-(N,N-dimethylaminocarbonyl)ethyl and 2-acetylaminoethyl and $R^7$ is methyl or ethyl when all of $Z^1$ to $Z^6$ represent a carbon atom. Particularly preferably, $R^7$ is methyl. Further, when $Z^2$ is a nitrogen atom and $Z^1$ and $Z^3$ to $Z^6$ represent a carbon atom, $R^6$ may be absent and $R^7$ may be methyl, ethyl, methoxy or the like, with methyl being preferred.

The "substituent" which may exist on the "optionally substituted $—(CH_2)_n$-phenyl group" is a hydroxyl group, a halogen atom, a trifluoromethyl group, a $(C_1-C_6)$alkyl group, a $(C_1-C_6)$alkoxy group, a $(C_1-C_6)$acyl group, $NR^4R^{4'}$, $NHCO(C_1-C_6)$alkyl, $NHCH_2C_6H_5$, $NHSO_2(C_1-C_6)$alkyl, $NHSO_2CH_2C_6H_5$, a nitro group or a cyano group. The number of the substituents on the phenyl group is from 1 to 5, and preferably from 1 to 2. Although the position of substitution is not particularly limited, the position is preferably meta-position with respect to $(CH_2)_n$. Preferred examples of the substituent include a methoxy group and a hydroxyl group.

Further, $R^4$ and $R^{4'}$ contained in $R^3$, $R^9$ and the substituent on the optionally substituted $—(CH_2)_n$—phenyl group are as defined above and may be the same or different. Likewise, $R^5$ contained in $R^3$, $R^8$ and $R^9$ is as defined above and may be the same or different.

When R and/or R is an imidazolyl, triazolyl or tetrazolyl, one or more ring carbon atoms of the each heterocyclic ring may be independently optionally substituted with one or more substituents which are independently selected from a hydrogen atom, a $(C_1-C_6)$alkyl group optionally substituted with one or more halogen atoms, a halogen atom, nitro, cyano and $—(CH_2)_n—R^9$ wherein $R^9$ is as defined above. In this connection, the aforementioned term "one or more substituents" means "from 1 to a" substituents wherein a is defined as the number of all positions on which a substituent can exist (i.e. the number of substituents when wholly substituted). Although the position of each substituent and the combination of substituents are not limited, preference is given to the case in which there is no substituent (i.e. all of the substituents being a hydrogen atom) or to the case in which there are two or more substituents and one of them is a halogen atom or a methyl group and the others are hydrogen atoms.

X represents an oxygen atom, a sulfur atom or $NR^{10}$ wherein $R^{10}$ represents a hydrogen atom, an optionally substituted $—(CH_2)_n$—phenyl group, a $—(C_1-C_{10})$alkyl group or a $—(CH_2)_n—R^8$ wherein $R^8$ is as defined above, with NH, an oxygen atom or a sulfur atom being preferred. Further, X is more preferably NH. The abovementioned n is an integer of from 0 to 6, and preferably of from 0 to 3.

Y represents an oxygen atom, NH, a sulfur atom or a methylene group, with an oxygen atom, NH or a sulfur atom being preferred. Further, Y is more preferably an oxygen atom or NH.

In the general formula (I) set forth above, *1 is an asymmetric carbon atom, and *2 is also an asymmetric carbon atom when $R^5$ is a $(C_1-C_6)$alkyl group. In such a case, the compound of the general formula (I) can be in the form of four isomers, that is to say (R,R), (R,S), (S,S) and (S,R) which are 6ach described in order of *1 and *2. When R5 is a hydrogen atom, two isomers can exist. Not only optically pure isomers, but also mixtures of two isomers with any mixing ratio encompassed by the present invention. Further, optional mixtures of three isomers and the mixture of all the four isomers are also encompassed by the present invention. From the viewpoint of the expression of pharmacological activity, a preferred configuration of the asymmetric carbon *1 is the configuration R.

In addition, illustrative examples of specific compounds of the present invention represented by the general formula (I) wherein $Z^1$ represents a carbon atom or a nitrogen atom and $Z^2$ to $Z^6$ represent a carbon atom, include:

ethyl (R)-6-[2-[2-(3-methylsulfonylamino)phenyl-2-hydroxyethylamino]ethoxy]-3-methyl-1H-indole-2-carboxylate;

(R)-6-[2-[2-(3-methylsulfonylamino)phenyl-2-hydroxyethylamino]ethoxy]-3-methyl-1H-indole-2-carboxylic acid;

ethyl (R)-6-[2-[2-(3-methylsulfonylamino)phenyl-2-hydroxyethylamino]ethoxy]-2-methyl-1H-indole-3-carboxylate;

(R)-6-[2-[2-(3-methylsulfonylamino)phenyl-2-hydroxyethylamino]ethoxy]-2-methyl-1H-indole-3-carboxylic acid;

(R)-N-[3-[2-[2-(3-hydroxymethyl-2-methyl-1H-indol-6-yloxy)ethylamino]-1-hydroxyethyl]phenyl]methanesulfonamide;

(R)-N-[3-[2-[2-[3-(N',N'-dimethylamino)methyl-2-methyl-1H-indol-6-yloxy]ethylamino]-1-hydroxyethyl]phenyl]methanesulfonamide;

ethyl (R)-[6-[2-[2-(3-methylsulfonylamino)phenyl-2-hydroxyethylamino]ethoxy]-2-methyl-1H-indol-3-yl]acetate;

(R)-[6-[2-[2-(3-methylsulfonylamino)phenyl-2-hydroxyethylamino]ethoxy]-2-methyl-1H-indol-3-yl]acetic acid;

ethyl (R)-3-[6-[2-[2-(3-methylsulfonylamino)phenyl-2-hydroxyethylamino]ethoxy]-2-methyl-1H-indol-3-yl]acrylate;

(R)-3-[6-[2-[2-(3-methylsulfonylamino)phenyl-2-hydroxyethylamino]ethoxy]-2-methyl-1H-indol-3-yl]acrylic acid;

ethyl (R)-3-[6-[2-[2-(3-methylsulfonylamino)phenyl-2-hydroxyethylamino]ethoxy]-2-methyl-1H-indol-3-yl]propionate;

(R)-3-[6-[2-[2-(3-methanesulfonylamino)phenyl-2-hydroxyethylamino]ethoxy]-2-methyl-1H-indol-3-yl]propionic acid;

(R)-N-[3-[2-[2-[3-(2-aminoethyl)-2-methyl-1H-indol-6-yloxy]ethylamino]-1-hydroxyethyl]phenyl]methanesulfonamide;

(R)-N-[3-[2-[2-[3-(2-N',N'-dimethylamino)ethyl-2-methyl-1H-indol-6-yloxy]ethylamino]-1-hydroxyethyl]phenyl]methanesulfonamide;

(R)-N-[3-[2-[2-[3-acetyl-2-methyl-1H-indol-6-yloxy]ethylamino]-1-hydroxyethyl]phenyl]methane sulfonamide;

ethyl (R)-[6-[2-[2-(3-methylsulfonylamino)phenyl-2-hydroxyethylamino]ethoxy]-2-ethyl-1H-indol-3-yl]acetate;

(R)-[6-[2-[2-(3-methylsulfonylamino)phenyl-2-hydroxyethylamino]ethoxy]-2-ethyl-1H-indol-3-yl]acetic acid;

ethyl (R)-[6-[2-[2-(3-methanesulfonylamino)phenyl-2-hydroxyethylamino]ethoxy]-2-phenyl-1H-indol-3-yl]acetate;

(R)-[6-[2-[2-(3-methylsulfonylamino)phenyl-2-hydroxyethylamino]ethoxy]-2-phenyl-1H-indol-3-yl]acetic acid;

ethyl (R)-[6-[2-[2-(4-chloro-3-methylsulfonylamino)phenyl-2-hydroxyethylamino]ethoxy]-2-methyl-1H-indol-3-yl]acetate;

(R)-[6-[2-[2-(4-chloro-3-methylsulfonylamino)phenyl-2-hydroxyethylamino]ethoxy]-2-methyl-1H-indol-3-yl]acetic acid;

ethyl (R)-[6-[2-[2-(4-fluoro-3-methylsulfonylamino)phenyl-2-hydroxyethylamino]ethoxy]-2-methyl-1H-indol-3-yl]acetate;

(R)-[6-[2-[2-(4-fluoro-3-methylsulfonylamino)phenyl-2-hydroxyethylamino]ethoxy]-2-methyl-1H-indol-3-yl]acetic acid;

(R)-[6-[2-[2-(4-hydroxy-3-methylsulfamoyl)phenyl-2-hydroxyethylamino]ethoxy]-2-methyl-1H-indol-3-yl]acetic acid;

(R)-[6-[2-[2-(3-methylsulfonylamino)phenyl-2-hydroxyethylamino]ethoxy]-2-(2-methoxyethyl)-1H-indol-3-yl]acetic acid;

(R)-3-[6-[2-[2-(3-methylsulfonylamino)phenyl-2-hydroxyethylamino]ethoxy]-2-(2-methoxyethyl)-1H-indol-3-yl]propionic acid;

(R)-N-[3-[2-[2-[2-(2-methoxyethyl)-3-methyl-1H-indol-6-yloxy]ethylamino]-1-hydroxyethyl]phenyl]methanesulfonamide;

(R)-N-[3-[2-[2-[3-ethyl-2-(2-methoxyethyl)-1H-indol-6-yloxy]ethylamino]-1-hydroxyethyl]phenyl]methanesulfonamide;

ethyl (R)-6-[2-[2-(3-methylsulfonylamino)phenyl-2-hydroxyethylamino]ethylamino]-3-methyl-1H-indole-2-carboxylate;

(R)-6-[2-[2-(3-methylsulfonylamino)phenyl-2-hydroxyethylamino]ethylamino]-3-methyl-1H-indole-2-carboxylic acid;

ethyl (R)-[6-[2-[2-(4-chloro-3-methylsulfonylamino)phenyl-2-hydroxyethylamino]ethoxy]-3-methyl-1H-indol-2-yl]acetate;

ethyl (R)-[6-[2-[2-(4-fluoro-3-methylsulfonylamino)phenyl-2-hydroxyethylamino]ethoxy]-3-methyl-1H-indol-2-yl]acetate;

ethyl (R,R)-6-[2-[2-(4-fluoro-3-methylsulfonylamino)phenyl-2-hydroxyethylamino]propoxy]-3-methyl-i 1H-indole-2-carboxylate;

ethyl (R)-6-[2-[2-(3-methylsulfonylamino)phenyl-2-hydroxyethylamino]ethoxy]-3-methyl-benzofuran-2-carboxylate;

(R)-6-[2-[2-(3-methylsulfonylamino)phenyl-2-hydroxyethylamino]ethoxy]-3-methyl-benzofuran-2-carboxylic acid;

ethyl (R)-[6-[2-[2-(3-methylsulfonylamino)phenyl-2-hydroxyethylamino]ethoxy]-2-methyl-benzofuran-3-yl]acetate;

(R)-[6-[2-[2-(3-methylsulfonylamino)phenyl-2-hydroxyethylamino]ethoxy]-2-methyl-benzofuran-3-yl]acetic acid;

ethyl (R)-[6-[2-[2-(3-methylsulfonylamino)phenyl-2-hydroxyethylamino]ethoxy]-2-phenylbenzothiophen-3-yl]acetate;

ethyl (R)-3-[6-[2-[2-(3-methylsulfonylamino)phenyl-2-hydroxyethylamino]ethoxy]-2-phenylbenzothiophen-3-yl]propionate;

(R)-N-[3-[2-[2-(2-pyrrolidylcarbonylbenzofuran-6-yloxy)ethylamino]-1-hydroxyethyl]phenyl]methanesulfonamide;

(R)-N-[3-[2-[2-[2-(isoxazol-3-yl)benzofuran-6-yloxy] ethylamino]-1-hydroxyethyl]phenyl]methanesulfonamide;

ethyl (R)-5-[2-[2-(3-methylsulfonylamino)phenyl-2-hydroxyethylamino]ethoxy]-3-methyl-1H-indole-2-carboxylate;

(R)-1-benzyl-6-[2-[2-(3-methylsulfonylamino)phenyl-2-hydroxyethylamino]ethoxy]-1H-indole-2-carboxylic acid;

(R)-1-[3-(N'-methylsulfonylamino)phenyl]methyl-6-[2-[2-(3-methylsulfonylamino)phenyl-2-hydroxyethylamino] ethoxy]-1H-indole-2-carboxylic acid;

(R)-1-[4-(N'-methylsulfonylamino)phenyl]methyl-6-[2-[2-(3-methylsulfonylamino)phenyl-2-hydroxyethylamino] ethoxy]-1H-indole-2-carboxylic acid;

(R)-N-[3-[2-[2-(2,3-ditrifluoromethyl-1H-indol-6-yloxy) ethylamino]-1-hydroxyethyl]phenyl]methanesulfonamide;

(R)-N-[3-[1-hydroxy-2-[2-(3-methyl-2-pyridin-3-yl-1H-indol-6-yloxy)ethylamino]ethyl]phenyl]methanesulfonamide;

(R)-N-[3-[2-[2-(3-ethyl-2-pyridin-3-yl-1H-indol-6-yloxy)ethylamino]-1-hydroxyethyl]phenyl]methanesulfonamide;

(R)-N-[3-[1-hydroxy-2-[2-(3-methyl-2-pyridin-4-yl-1H-indol-6-yloxy)ethylamino]ethyl]phenyl]methanesulfonamide;

(R)-N-[3-[2-[2-[2-(N'-t-butyloxycarbonylpiperidin-3-yl)-3-methyl-1H-indol-6-yloxy]ethylamino]-1-hydroxyethyl] phenyl]methanesulfonamide;

(R)-N-[3-[2-[1-hydroxy-2-(3-methyl-2-piperidin-3-yl-1H-indol-6-yloxy)ethylamino]ethyl]phenyl]methanesulfonamide;

(R)-N-[3-[2-[2-[3-(2-acetylaminoethyl)-2-methyl-1H-indol-6-yloxy]ethylamino]-1-hydroxyethyl]phenyl]methanesulfonamide;

ethyl (R)-3-[6-[2-[2-hydroxy-2-(3-methylsulfonylaminophenyl)ethylamino]ethoxy]-3-phenyl-1H-indol-2-yl]propionate;

(R)-N-[2-fluoro-5-[1-hydroxy-2-[2-(3-methyl-2-pyridin-3-yl-1H-indol-6-yloxy)ethylamino]ethyl]phenyl]methanesulfonamide;

ethyl (R)-3-[6-[2-[2-(4-fluoro-3-methylsulfonylaminophenyl)-2-hydroxyethylamino]ethoxy]-3-methyl-1H-indol-2-yl]propionate;

(R)-3-[3-methyl-6-[2-[2-(3-methylsulfonylaminophenyl)-2-hydroxyethyl]amino]ethoxy]-1H-indol-2-yl]-N,N-dimethylpropionamide;

ethyl (R)-3-[3-methyl-6-[2-[2-(3-methylsulfonylaminophenyl)-2-hydroxyethylamino]ethoxy]-1H-indol-2-yl] propionate; and ethyl (R)-2-[3-methyl-6-[2-[2-(3-methylsulfonylaminophenyl)-2-hydroxyethylamino]ethoxy]-1H-indol-2-yl]acetate.

Further, illustrative examples of specific compounds of the present invention represented by the general formula (I) wherein $Z^2$ represents a nitrogen atom and $Z^1$ and $Z^3$ to $Z^6$ represent a carbon atom, include:

(R)-N-[3-[2-[2-(3-methylindazol-6-yloxy)ethylamino]-1-hydroxyethyl]phenyl]methanesulfonamide;

(R)-N-[3-[2-[2-(1-benzyl-3-methylindazol-6-yloxy)ethylamino]-1-hydroxyethyl]phenyl]methanesulfonamide;

(R)-N-[3-[2-[2-(3-methoxyindazol-6-yloxy)ethylamino]-1-hydroxyethyl]phenyl]methanesulfonamide;

(R)-N-[5-[2-[2-(3-methylindazol-6-yloxy)ethylamino]-1-hydroxyethyl]-2-fluorophenyl]methanesulfonamide;

(R)-N-[5-[2-[2-(3-methylindazol-6-yloxy)ethylamino]-1-hydroxyethyl]-2-chlorophenyl]methanesulfonamide;

(R)—N-methyl-[5-[2-[2-(3-methylindazol-6-yloxy)ethylamino]-1-hydroxyethyl]-2-hydroxybenzenesulfonamide; and (R,R)-N-[3-[1-hydroxy-2-[1-methyl-2-(3-methylindazol-6-yloxy)ethylamino]ethyl]phenyl]methanesulfonamide.

Processes for the preparation of compounds represented by the general formula (I) are illustrated in the following.

[Preparation Process 1]

Compounds of the general formula (I) may be prepared according to the processes described in WO 97/25311 and WO 00/58287. That is, an objective compound of the general formula (I) may be prepared by, as the first step, reacting a compound represented by the general formula (II):

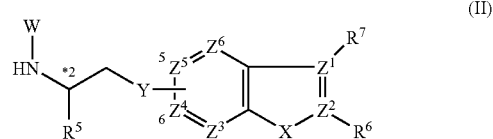

wherein W represents a hydrogen atom or an amino-protecting group, and $R^5$, $R^6$, $R^7$, X, Y, $Z^1$ to $Z^6$ and *2 are each as defined above, with a compound represented by the general formula (III):

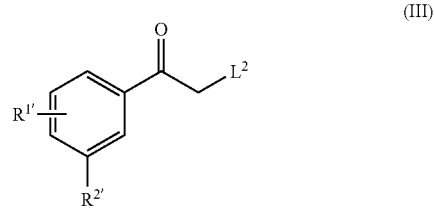

wherein $R^{1'}$ represents a hydrogen atom, $OA^1$ (wherein $A^1$ represents a hydroxyl-protecting group) or a halogen atom, $R^{2'}$ represents $NW^2SO_2R^3$ or $SO_2NR^4R^{4'}$, $W^2$ represents a hydrogen atom or an amino-protecting group, $L^2$ represents a leaving group, and $R^3$, $R^4$ and $R^{4'}$ are each as defined above, to give an amino ketone (—CO—$CH_2$—NW—); as the second step, reducing the thus obtained amino ketone compound to give an amino alcohol (—CHOH—$CH_2$—NW—) compound; and, as the final step, optionally removing the hydroxyl-protecting group $A^1$ on the benzene ring and, when W and $W^2$ are not hydrogen atoms but amino-protecting groups, removing them. Examples of $L^2$ include a chlorine atom, a bromine atom, an iodine atom and the like. When W and $W^2$ represent an amino-protecting group, the amino-protecting group is not limited as long as it is a protecting group used in a common organic synthesis. Preferred examples of the amino-protecting group include a benzyl group, a substituted benzyl group and the like. When $R^1$ is $OA^1$, the hydroxyl-protecting group $A^1$ is also not limited as long as it is a protecting group used in a common organic synthesis. Preferred examples of the hydroxyl-protecting group include a benzyl group, a substituted benzyl group and the like.

The amount of the compound represented by the general formula (II) to be used in the first step is from 1 to 5 mol for 1 mol of the compound represented by the general formula (III). A base may be added to neutralize an acid generated by the reaction. Examples of the base to be used include organic bases such as triethylamine, diisopropylethylamine and pyridine, inorganic bases such as potassium carbonate, sodium hydrogencarbonate and sodium hydroxide and the like. Further, compounds of the general formula (II) may be used also in the form of their salts, provided that the abovementioned base is added.

Examples of the solvent to be used in the reaction include lower alcohols such as methanol, ethanol and isopropyl alcohol, chlorinated hydrocarbons such as methylene chloride, chloroform and 1,2-dichloroethane, tetrahydrofuran, dimethylformamide, dimethylsulf oxide and the like, with dimethylformamide being preferred. Although reaction temperatures and reaction times are not limited, the reaction is carried out at a temperature of from −30° C. to the boiling point of the selected solvent, preferably a temperature of from 0° C. to 30° C., for 10 minutes to 24 hours.

The amino ketone generated in the first step may be used in the reductive reaction of the second step without isolation from the reaction mixture. However, the amino ketone may be optionally extracted and purified before the reductive reaction. Examples of the reducing agent to be used include sodium borohydride, sodium cyanoborohydride, borane and the like. Examples of the solvent to be used in the reaction include lower alcohols such as methanol, ethanol and isopropyl alcohol, tetrahydrofuran, dimethylformamide, dimethylsulfoxide and the like, with ethanol and dimethylformamide being preferred. Although reaction temperatures and reaction times are not limited, the reaction is carried out at a temperature of from −30° C. to the boiling point of the selected solvent, preferably a temperature of from 0° C. to 30° C., for 10 minutes to 24 hours.

When the removal of the amino-protecting group and/or hydroxyl-protecting group is needed as the final step, they may be removed under reaction conditions usually used for removing the protecting groups to be used. When a benzyl or substituted benzyl group is used as the protecting group, it may be removed, for example, by a hydrogenation reaction using palladium/activated carbon as a catalyst.

Compounds represented by the general formula (I), which contain asymmetric carbons represented by *1 and *2, are obtained as a racemic mixture by the process set forth above. The racemic mixture can be optically resolved into optically active substances by converting the racemic mixture to acid addition salts with an optically active acid such as camphorsulfonic acid or mandelic acid followed by a fractional crystallization treatment. The racemic mixture may be also optically resolved using a commercially available optically active column.

Further, optically active substances may be also obtained by carrying out an asymmetric reduction treatment with a hydrogen donating compound in the presence of an asymmetric reduction catalyst in the second step according to the process described in WO 00/58287.

[Preparation Process 2]

Compounds of the general formula (I) may be also prepared by another process set forth below according to the processes described in WO 97/25311 and WO 01/04092. That is, an objective compound of the general formula (I) may be prepared by, as the first step, reacting a compound represented by the general formula (TI) with a compound represented by the general formula (IV)

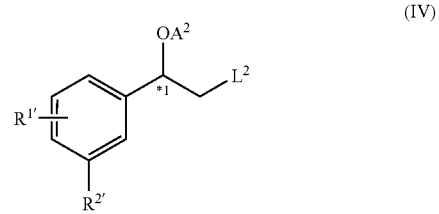

wherein $L^2$ represents a leaving group, $A^2$ represents a hydroxyl-protecting group, and R1', R2' and *1 are as defined above, to give an amino ether (—CHO$A^2$—CH$_2$—NHW—) compound; and, as the second step, removing the hydroxyl-protecting group $A^2$, optionally removing the hydroxyl-protecting group $A^1$, and when W and $W^2$ are not hydrogen atoms but amino-protecting groups, removing them. Examples of the leaving group $L^2$ include a chlorine atom, a bromine atom, an iodine atom and the like, with an iodine atom being preferred. W and $W^2$ are as set forth above in Preparation Process 1. The hydroxyl-protecting group $A^1$ when $R^{1'}$ is $OA^1$ is also as set forth above in Preparation Process 1. Another hydroxyl-protecting group $A^2$ is also not limited as long as it is a protecting group used in a common organic synthesis. Preferred examples of the hydroxyl-protecting group include a triethylsilyl group.

The amount of the compound represented by the general formula (II) to be used is from 1 to 1.5 mol for 1 mol of the compound represented by the general formula (IV). A base may be added to neutralize an acid generated by the reaction. Examples of the base to be used include triethylamine, diisopropylethylamine and the like. Further, compounds of the general formula (II) may be used also in the form of their salts, provided that the abovementioned base is added.

Examples of the solvent to be used in the reaction include dimethylformamide, dimethylacetamide, dimethylsulfoxide and the like, with dimethylformamide being preferred. Although reaction temperature and reaction time are not limited, the reaction is carried out at a temperature of from 0° C. to 90° C., preferably a temperature of 60° C., for 10 minutes to 24 hours. The hydroxyl-protecting group $A^2$ and optionally the other protecting groups may be removed under reaction conditions usually used for removing the protecting groups to be used. A triethylsilyl group as $A^2$ may be removed using, for example, tetrabutylammonium fluoride.

Optically active substances may be prepared as set forth above in Preparation Process 1 by formation of acid addition salts with an optically active acid followed by a fractional crystallization treatment, or optical resolution using a commercially available optically active column or the like.

Further, an optically active compound represented by the general formula(I) may be also prepared using an optically active compound represented by the general formula (IV) prepared according to the processes described in, for example, WO 97/25311 and WO 01/04092, and a compound represented by the general formula (II) wherein $R^5$ is a hydrogen atom.

[Preparation Process 3]

Compounds of the general formula (I) may be also prepared by another process set forth below according to the process described in WO 01/04092. That is, an objective compound of the general formula (I) may be prepared by reacting a compound represented by the general formula (V):

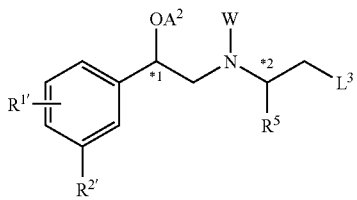

(V)

wherein L³ represents a hydroxyl group or a leaving group, and R¹', R²', R⁵, A², W, *1 and *2 are as defined above, with a compound represented by the general formula (VI):

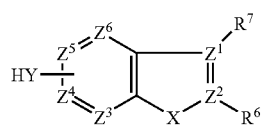

(VI)

wherein Y represents an oxygen atom or a sulfur atom, and R⁶, R⁷, X and Z¹ to Z⁶ are as defined above; and, as the second step, removing the hydroxyl-protecting group A², optionally removing the hydroxyl-protecting group A¹, and when W and W² are not hydrogen atoms but amino-protecting groups, removing them.

Examples of the leaving group L³ include a chlorine atom, a bromine atom, an iodine atom and the like, with bromine atom being preferred.

Compounds represented by the general formula (III) are known compounds and may be prepared by the process described in, for example, WO 97/25311 or the literature (J. Med. Chem., vol. 10, p. 462 (1966)). Further, compounds represented by the general formula (IV) are known compounds and may be prepared by the process described in, for example, WO 97/25311. Further, compounds represented by the general formula (V) are known compounds and may be prepared by the process described in, for example, WO 01/04092.

Compounds represented by the general formula (II) are characteristic of important intermediates for synthesizing compounds represented by the general formula (I) and are novel compounds except that R⁵ represents a (C₁-C₆)alkyl group and both of R⁶ and R⁷ represent a hydrogen atom. Processes for the preparation of compounds represented by the general formula (II) are illustrated in the following.

[Preparation Process a]

Compounds represented by the general formula (II) wherein Y is an oxygen atom may be prepared by the process set forth below. That is, an objective compound may be obtained by reacting a compound represented by the general formula (VI):

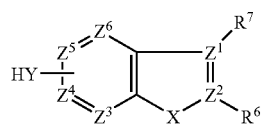

(VI)

wherein Y represents an oxygen atom, and R⁶, R⁷, X and Z¹ to Z⁶ are as defined above, with a compound represented by the general formula (VII):

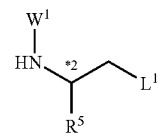

(VII)

wherein L¹ represents a leaving group, W¹ represents an amino-protecting group, and R⁵ and *2 are as defined above, in the presence of a base; as the second step, removing the amino-protecting group W¹; and, as the final step, optionally re-protecting this amino group with another protecting group W. Even if W is a hydrogen atom (i.e. the amino group is in the free form), the compound may be used in the following reaction. Examples of the leaving group L¹ include a chlorine atom, a bromine atom, an iodine atom and the like. The amino-protecting group W¹ is not limited as long as it is a protecting group used in a common organic synthesis. Preferred examples include a benzyloxycarbonyl group, a substituted benzyloxycarbonyl group, a tert-butoxycarbonyl group and the like. W may be selected as set forth above in Preparation Process 1 for compounds of the formula (I).

The amount of the compound represented by the general formula (VII) to be used in the first step is from 1 to 5 mol for 1 mol of the compound represented by the general formula (VI). Examples of the base to be used include potassium carbonate, sodium carbonate, potassium hydroxide, sodium hydroxide, sodium hydride, sodium methoxide, triethylamine and the like. Examples of the solvent to be used in the reaction include tetrahydrofuran, dimethyl formamide, dimethylacetamide, dimethyl sulfoxide, acetonitrile and the like. Although reaction temperature and reaction time are not limited, the reaction is carried out at a temperature of from 0° C. to the boiling point of the selected solvent, preferably from room temperature to 90° C., for 10 minutes to 24 hours. methoxide, triethylamine and the like. Examples of the solvent to be used in the reaction include tetrahydrofuran, dimethylformamide, dimethylacetamide, dimethylsulfoxide, acetonitrile and the like. Although reaction temperature and reaction time are not limited, the reaction is carried out at a temperature of from 0° C. to the boiling point of the selected solvent, preferably a temperature of from room temperature to 90° C., for 10 minutes to 24 hours.

In the second step, the amino-protecting group W¹ may be removed under reaction conditions usually used for removing the protecting group to be used. When a benzyloxycarbonyl or substituted benzyloxycarbonyl group is used as the protecting group, it may be removed, for example, by a hydrogenation reaction using palladium/activated carbon as a catalyst. When a tert-butoxycarbonyl group is used as the protecting group, it may be removed using an acid such as trifluoroacetic acid or hydrochloric acid.

[Preparation Process b]

Compounds represented by the general formula (II) wherein Y is a sulfur atom may be prepared by the process set forth below. That is, an objective compound may be obtained by reacting a compound represented by the general formula (VI):

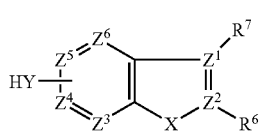
(VI)

wherein Y represents a sulfur atom, and $R^6$, $R^7$, X and $Z^1$ to $Z^6$ are as defined above, with a hydrochloride or hydrobromide salt of a compound represented by the general formula (VII):

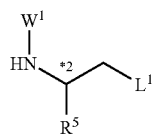
(VII)

wherein $W^1$ represents a hydrogen atom, $L^1$ represents a chlorine atom or a bromine atom, and $R^5$ and *2 are as defined above.

The amount of the compound represented by the general formula (VII) to be used is from 1 to 1.5 mol for 1 mol of the compound represented by the general formula (VI). The reaction is usually carried out in the presence of a base. Examples of the base include organic bases such as triethylamine, diisopropylethylamine and pyridine, inorganic bases such as potassium carbonate, sodium hydrogencarbonate and sodium hydroxide and the like. Examples of the solvent to be used in the reaction include lower alcohols such as methanol, ethanol and isopropyl alcohol, acetic acid, chlorinated hydrocarbons such as methylene chloride, chloroform and 1,2-dichloroethane, tetrahydrofuran, dimethylformamide, dimethylsulfoxide and the like, which may be used alone or as a mixed solvent comprising plural solvents. Preferably, a mixed solvent of tetrahydrofuran and methanol is used. Although reaction temperature and reaction time are not limited, the reaction is carried out at a temperature of from −30° C. to the boiling point of the selected solvent, preferably a temperature of from 0° C. to 30° C., for 10 minutes to 24 hours.

[Preparation Process c]

Compounds represented by the general formula (II) wherein Y is NH may be prepared by the process set forth below. That is, as the first step, a triflate compound represented by the general formula (VIII):

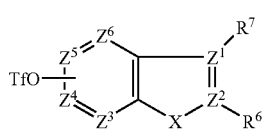
(VIII)

wherein $R^6$, $R^7$, X and $Z^1$ to $Z^6$ are as defined above, is reacted with a compound represented by the general formula (IX):

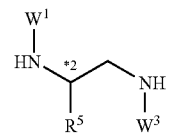
(IX)

wherein $W^1$ and $W^3$ each represent an amino-protecting group, and $R^5$ and *2 are as defined above. This reaction can be carried out according to the process described in the literature (B. H. Yang et al., *Journal of Organometallic Chemistry*, 576, pp. 125-146, 1999).

And then, a compound represented by the general formula (II'):

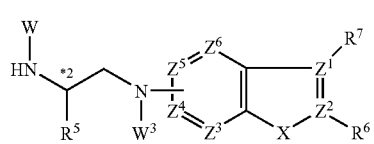
(II')

wherein $R^5$, $R^6$, $R^7$, X, $Z^1$ to $Z^6$, W and $W^3$ are as defined above, may be obtained by, as the second step, removing the amino-protecting group $W^1$, and, as the final step, optionally re-protecting this amino group with another protecting group W.

The triflate compound of the general formula (VIII) may be obtained by applying reaction conditions commonly used for converting a hydroxyl group into a triflate group to a compound of the general formula (VI) wherein Y is an oxygen atom. The amino-protecting group $W^1$ is not limited as long as it is a protecting group used in a common organic synthesis. Preferred examples include a benzyloxycarbonyl group, a substituted benzyloxycarbonyl group, a tert-butoxycarbonyl group and the like. The amino-protecting group $W^3$ is not limited as long as it is a protecting group used in a common organic synthesis. Preferred examples include a benzyl group, a substituted benzyl group and the like. The compound having the amino-protecting group $W^3$ is more preferably provided for the next reaction in the protected form without removing the amino-protecting group $W^3$ than in the form of free amine obtained by removing the amino-protecting group $W^3$. The compound in which W is a hydrogen atom (i.e. the amino group being in the free form) can be also provided for the next reaction. W may be selected as set forth above in Preparation Process 1 for compounds of the general formula (I). In the second step, the amino-protecting group $W^1$ may be removed under reaction conditions usually used for removing the protecting group to be used.

[Preparation Process d]

Compounds represented by the general formula (II) wherein Y is a methylene group may be prepared by or according to the known process described in the literature (Troxler et al., *Helv. Chim. Acta.*, vol. 51, p. 1616, 1968) or WO 94/29290. Further, other compounds represented by the general formula (II) wherein Y is a methylene group may be also prepared according to the known process for preparing indole derivatives, the known process for preparing benzofuran derivatives or the known process for preparing benzothiophene derivatives.

Then, compounds represented by the general formula (VI):

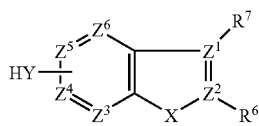

wherein Y represents an oxygen atom or a sulfur atom, and $R^6$, $R^7$, X and $Z^1$ to $Z^6$ are as defined above, may be prepared by or according to the known processes set forth below.

[Preparation Process i]

Namely, compounds represented by the general formula (VI) set forth above wherein $R^7$ represents a hydrogen atom or a ($C_1$-$C_6$)alkyl group optionally substituted with one or more halogen atoms may be synthesized according to the process described in WO 94/29290.

[Preparation Process ii]

Then, compounds represented by the general formula (VI) wherein Y represents an oxygen atom and $Z^1$ to $Z^6$ represents a carbon atom may be synthesized by the process indicated in the following reaction scheme.

Namely, a compound represented by the general formula (X):

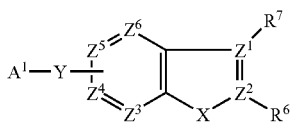

wherein $Z^1$ to $Z^6$ represent a carbon atom, $R^7$ represents a hydrogen atom, Y represents an oxygen atom, $A^1$ represents a hydroxyl-protecting group, and X and $R^6$ are as defined above, is formylated via a Vilsmeyer reaction to give a compound represented by the general formula (XI):

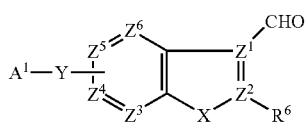

wherein $R^6$, X, Y, $Z^1$ to $Z^6$ and $A^1$ are each as defined above; then, $R^7$ is introduced by subjecting the resulting formyl group to a reaction commonly used in organic chemical reactions, to give a compound represented by the general formula (XII):

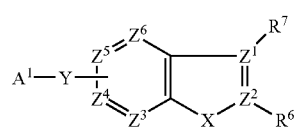

wherein $R^6$, $R^7$, X, Y, $Z^1$ to $Z^6$ and $A^1$ are each as defined above. Finally, a compound represented by the general formula (VI) may be obtained by removing the protecting group $A^1$ under a commonly used condition.

A compound represented by the general formula (X) may be commercially available, or may be synthesized by the process described in WO 94/29290 or according to the processes described in the following literatures.

That is, a compound represented by the general formula (X) wherein X=NH, Y=O, $Z^1$ represents a nitrogen atom or a carbon atom, $Z^2$ to $Z^6$ represent a carbon atom and $R^6$=an alkyl group or an aryl group may be synthesized by the process described in the literature (Mentzer et al., *Bull. Soc. Chim. Fr.*, p. 555, p. 559, 1950) or the literature (E. von Angerer et al., *J. Med. Chem.*, vol. 27, No. 25, pp. 1439-1447, 1984). Likewise, a compound represented by the general formula (X) wherein X=O, Y=O, $Z^1$ represents a nitrogen atom or a carbon atom, $Z^2$ to $Z^6$ represent a carbon atom and $R^6$=an alkyl group may be synthesized by the process described in the literature (G. Pandey et al., *Tetrahedron Lett.*, vol. 30, No. 14. pp. 1867-1870, 1989). A compound represented by the general formula (X) wherein, X=S, Y=O, $Z^1$ represents a nitrogen atom or a carbon atom, $Z^2$ to $Z^6$ represent a carbon atom and $R^6$=an aryl group may be synthesized by the process described in the literature (Fries et al., *Justus Liebigs Ann. Chem.*, vol. 527, p. 83-114, 1937) or the literature (E. von Angerer et al., *J. Steroid Biochem. Mol. Biol.*, vol. 41, pp. 557-562). A compound represented by the general formula (X) wherein X=NH, Y=O, $Z^2$ represents a nitrogen atom, $Z^1$ and $Z^3$ to $Z^6$ represent a carbon atom and $R^7$=an alkyl group may be synthesized by the process described in the literature (S. Caron et al., *Synthesis*, No. 4, pp. 588-592, 1999) or the literature (Davies et al., *J. Chem. Soc.*, pp. 2412-2419, 1955). A compound represented by the general formula (X) wherein X=NH, Y=NH, $Z^2$ represents a nitrogen atom, $Z^1$ and $Z^3$ to $Z^6$ represent a carbon atom and $R^7$=an alkyl group may be synthesized by the process described in the literature (Davies et al., *J. Chem. Soc.*, pp. 2412-2419, 1955).

In addition, a compound represented by the general formula (XI) may be synthesized by the process described in the literature (R. Gastpar et al., *J. Med. Chem.*, vol. 41, No. 25, pp. 4965-4972, 1998) or the literature (K. Cardwell et al., *J. Am. Chem. Soc.*, vol. 110, pp. 2242-2248, 1988).

The present compounds and the starting compounds and intermediates for preparing each of the present compounds which can be obtained as set forth above may be isolated and purified by the conventional means such as extraction, crystallization, distillation, chromatography, recrystallization or the like.

Salts of a compound of the general formula (I) according to the present invention may be a known salt, and examples thereof include hydrochloride, hydrobromide, sulfate, hydrogensulfate, dihydrogen phosphate, citrate, maleate, tartrate, fumarate, gluconate, methanesulfonate and the like, and acid addition salts with an optically active acid such as camphorsulfonic acid, mandelic acid or substituted mandelic acid. Among them, pharmaceutically acceptable salts are particularly preferred.

When a compound of the general formula (I) is converted into its salt, an acid addition salt of the compound can be obtained by dissolving the compound in alcohol such as methanol or ethanol, to which the equivalent amount to several times amount of the acid component is then added. The acid component to be used may be a pharmaceutically acceptable mineral or organic acid, such as hydrochloric acid, hydrobromic acid, sulfuric acid, hydrogensulfate, dihydrogen phosphate, citric acid, maleic acid, tartaric acid, fumaric acid, gluconic acid or methanesulfonic acid.

Compounds of the present invention and pharmaceutically acceptable salts thereof, which have no recognizable toxic effect, are useful as a medicines. For example, the compounds, which have β3-receptor agonist activities, can be used as a medicine for treating and preventing β3-receptor associated diseases. The term "β3-receptor associated disease" is a generic term directed to diseases which can be improved by agonistic effects mediated by the receptor. Examples of β3-receptor associated diseases include diabetes, obesity, hyperlipidemia, fatty liver, digestive diseases (preferably dyskinesia of digestive system or ulcer) and depression. In addition, the compound can be used as a medicine for treating and preventing fatty liver, urinary incontinence and others.

Urinary incontinence is defined by International Incontinence Society as a condition in which involuntary urine loss is a social or hygienic problem and is objectively demonstrable.

Compounds of the present invention are safe compounds with a low acute toxicity. Further, compounds of the present invention are characterized, for example, in that they do not inhibit some of drug metabolizing enzymes (cytochrome P-450). Methods for determining whether cytochrome P-450 may be inhibited or not include known methods described, for example, in the literature (Crespi C. L. et al., *Analytical Biochemistry*, vol. 248, pp. 188-190, 1997).

Even compounds of the present invention and pharmaceutically acceptable salts thereof obtained by a synthetic means have β3-receptor agonistic effects, and those generated as a result of an in vivo metabolism also have the same β3-receptor agonistic effects. Therefore, compounds which generate the present compound as a result of an in vivo metabolism are also useful as medicines.

A medicine of the present invention is preferably prepared in the form of a pharmaceutical composition by optionally adding a pharmaceutically acceptable carrier to an effective amount of a compound represented by the general formula (I) or a salt thereof. Examples of pharmaceutically acceptable carriers include excipients, binders such as carboxymethylcellulose, disintegrators, lubricants, auxiliaries and the like.

When a compound of the present invention is administered to humans, it can be orally administered in the form of tablet, powder, granule, capsule, sugar-coated tablet, solution, syrup or the like. Further, it can be parenterally administered in the form of injection or the like. Although the dosage will vary dependent on the age and weight of the patient and the extent of disease, the daily dosage for an adult is usually from 0.01 to 2000 mg, which is singly administered or is divided into several dosages and then administered. The duration of administration can vary between several weeks and several months and the everyday medication is usually applied. However, the daily dosage and duration of administration can be increased or decreased from the above ranges dependent on the conditions of patient.

The disclosures in the text of specification of Japanese Patent Application No. 2001-327467, from which the present application claims the priority right, are incorporated herein.

DESCRIPTION OF PREFERRED
EMBODIMENTS OF THE INVENTION

The following Examples, Reference Examples and Test Examples specifically illustrate this invention but are not intended to limit it in any way.

In the following examples, each analysis was carried out as follows.

(1) Fast Atom Bombardment Mass Spectrum (FAB-MS)

Fast atom bombardment mass spectrum was determined with a JMS-AX500 type mass spectrometer manufactured by JEOL. LTD or a JMS-SX102 type mass spectrometer manufactured by JEOL. LTD. The matrix used was 3-nitrobenzyl alcohol.

(2) Liquid Chromatography-Mass Spectrometry (LC-MS)

The mass spectrometer used was a Platform-LC type mass spectrometer manufactured by Micromassm (England). A compound to be analyzed was ionized by erectrospray (ESI) method. The liquid chromatograph used was that manufactured by GILSON (France). The separation column used was Mightysil RP-18 GP 50-4.6 (product number 25468-96) manufactured by KANTO KAGAKU (Japan). The eluting conditions are as follows.

Flow rate: 2 mL/min;
Solvent:
Liquid A=water containing 0.1%(v/v) acetic acid;
Liquid B=acetonitrile containing 0.1%(v/v) acetic acid;
A linear gradient of 5-100%(v/v) Liquid B over 5 minutes (from 0 to 5 min) was used.
Elution time was indicated by "minute".

(3) Proton Nuclear Magnetic Resonance ($^1$H-NMR) Spectrum

The determination of proton nuclear magnetic resonance spectrum was carried out using a Gemini-300 type nuclear magnetic resonance apparatus manufactured by Varian (U.S.A.). Tetramethylsilane was used as the internal standard and chemical shift was indicated in δ (ppm). In this connection, the splitting patterns were indicated using the following abbreviations.

| | |
|---|---|
| s: singlet; | d: doublet; |
| t: triplet; | q: quartet; |
| quintet: quintet; | m: multiplet; |
| dd: double doublet; | dt: double triplet; |
| brs: broad singlet. | |

(4) Thin Layer Chromatography (TLC)

The thin layer chromatography (TLC) used was TLC plate (silica gel 60 $F_{254}$, product number 1,05715) manufactured by Merck (Germany). The detection of a compound was carried out by developing the plate followed by irradiation with UV (254 nm).

(5) Purification Chromatography

A purifying process with silica gel column was carried out using silica gel 60 manufactured by Merck (Germany). An objective compound was eluted with a mixed solvent (n-hexane/ethyl acetate or chloroform/methanol).

A purifying process with reversed phase column was carried out using a YMC CombiPrep ODS-A CCAAS05-0520WT type column manufactured by YMC (Japan). An objective compound was eluted by gradient elution using water/acetonitrile (containing 0.1%(v/v) acetic acid). The detailed eluting conditions are as follows.

Flow rate: 20 mL/min;
Solvent:
Liquid A=water containing 0.1%(v/v) trifluoroacetic acid;
Liquid B=acetonitrile containing 0.1%(v/v) trifluoroacetic acid;
From 0 to 1 min: Liquid B was maintained at 5%(v/v).
From 1 to 11 min: A linear gradient of 5-50%(v/v) Liquid B was used.
From 11 to 16 min: A linear gradient of 50-100%(v/v) Liquid B was used.

The following abbreviations are used in Examples set forth below.
DMSO: dimethylsulfoxide
THF: tetrahydrofuran
DMF: dimethylformamide With respect to intermediates about which no preparing process and reference are described in Examples or Reference Examples, their chemical names and the literatures comprising described therein processes for preparing them are mentioned below.

N-(3-bromoacetylphenyl)methanesulfonamide (Larsen et al., *J. Med. Chem.*, vol. 9, pp. 88-97, 1966);

2-benzyloxy-5-bromoacetyl-N-methylbenzenesulfonamide (JP-A-9-249623);

N-(5-bromoacetyl-2-chlorophenyl)methanesulfonamide (JP-A-9-249623); and

N-(3-bromoacetyl-4-fluorophenyl)methanesulfonamide (WO 91/12236).

REFERENCE EXAMPLE 1

Synthesis of (R)-[3-[2-[N-benzyl-N-(2-hydroxyethyl)amino]-1-triethylsilyloxy]ethyl]phenyl](methylsulfonyl)benzylamine In accordance with the process described in Example 26 of WO 01/04092, the title compound (15.1 g) was obtained from N-benzylethanolamine (31.4 mL) and Compound 10 (17.6 g) which had been obtained according to the process described in Example 29 of the same patent publication.

$^1$H-NMR (CDCl$_3$): δ(ppm) 0.36-0.45 (6H, m), 0.79 (9H, t, J=7.8), 1.50-1.80 (1H, brs), 2.49-2.69 (3H, m), 2.71-2.80 (1H, m), 2.93 (3H, s), 3.37 (2H, t, J=5.4), 3.59 (1H, d, J=13.8), 3.66 (1H, d, J=13.8), 4.49 (1H, t, J=6.3), 4.80 (1H, d, J=14.4), 4.90 (1H, d, J=14.4), 7.11-7.35 (14H, m).

REFERENCE EXAMPLE 2

Synthesis of
N-(3-acetyl-4-chlorophenyl)methanesulfonamide 1-(5-Amino-2-chlorophenyl)ethanone (411 mg; synthesized by the process reported by Radziejewski et al., *Heterocycles*, vol. 26, pp. 1227-1238, 1987) was dissolved in toluene (5 mL), and pyridine(235 μL) and methanesulfonyl chloride (225 μL) were added. The resulting mixture was stirred at room temperature for 50 minutes. After adding water (50 mL), the reaction mixture was extracted with ethyl acetate (50 mL). The organic layer was washed with an aqueous 1 N hydrochloric acid solution (50 mL) and saturated brine (50 mL) and then dried over anhydrous sodium sulfate (5 g). The solvent was distilled off under reduced pressure to yield N-(3-acetyl-4-chlorophenyl)methanesulfonamide (595 mg) as a colorless crystal.

$^1$H-NMR (CDCl$_3$): δ(ppm) 7.43-7.33 (3H, m), 7.10 (1H, brs), 3.05 (3H, s), 2.67 (3H, s);
TLC (1:1 n-hexane/ethyl acetate): R$_f$=0.31;
LC-MS: elution time 3.1 minutes;
m/z=246(M−H)$^-$.

REFERENCE EXAMPLE 3

Synthesis of
N-(3-bromoacetyl-4-chlorophenyl)methanesulfonamide

N-(3-acetyl-4-chlorophenyl)methanesulfonamide (300 mg) was dissolved in dioxane (5 mL), and bromine (77 μL) was added dropwise with ice-cooling. After stirring at room temperature for 1 hour, the solvent was distilled off under reduced pressure. The residue was washed with a water/ethanol mixture (1:1) and then dried under reduced pressure to yield N-(3-bromoacetyl-4-chlorophenyl)methanesulfonamide (312 mg) as a colorless crystal.

$^1$H-NMR (CDCl$_3$): δ(ppm) 7.46-7.36 (3H, m), 6.90 (1H, brs), 4.52 (2H, s), 3.07 (3H, s);
TLC (4:1 n-hexane/ethyl acetate): R$_f$=0.31;
LC-MS: elution time 3.5 minutes;
m/z=324 (M−H)−.

REFERENCE EXAMPLE 4

Synthesis of
N-(3-acetyl-5-aminophenyl)methanesulfonamide

3-Amino-5-nitrobenzophenone (4 g; synthesized by the process reported by Berend et al., *J. Prakt. Chem.*, vol. 69, p. 471 (1904)) was dissolved in pyridine (40 mL), and the temperature was maintained at 50° C. Methanesulfonyl chloride (1.9 mL) was added, followed by stirring for 2 hours. Additional methanesulfonyl chloride (1.7 mL) was added, followed by stirring at 50° C. for 2 hours. The reaction mixture was cooled down to room temperature and then poured into water (200 mL). The deposited precipitate was collected by filtration and dried under reduced pressure to yield N-(3-acetyl-5-nitrophenyl)methanesulfonamide (5.4 g) as a crude product. The whole quantity of the crude product was dissolved in ethanol (40 mL), and zinc dust (20 g) was added. After further adding concentrated hydrochloric acid (2 mL), the mixture was heated to reflux for 4 hours. The reaction mixture was filtered. To the filtrate, ethyl acetate (100 mL) was added. The resulting mixture was washed with water (100 mL) three times and the organic layer was dried over anhydrous magnesium sulfate. The solvent was distilled off under reduced pressure and the residue was purified by silica gel column chromatography (95:5 chloroform/methanol) to yield N-(3-acetyl-5-aminophenyl)methanesulfonamide (3.9 g).

$^1$H-NMR (DMSO-d$_6$); δ(ppm) 8.27 (1H, brs), 6.96 (1H, m), 6,93 (1H, m), 6.71 (1H, m);
TLC (10:1 chloroform/methanol): R$_f$=0.55;
FAB-MS: m/z=229 (M+H)$^+$.

REFERENCE EXAMPLE 5

Synthesis of
N-(3-acetyl-5-chlorophenyl)methanesulfonamide

Sodium nitrite (0.34 g) was added in three portions to concentrated sulfuric acid (3.5 mL). After the addition was completed, the solution was stirred at 70° C. for 10 minutes to dissolve the sodium nitrite completely. The resulting solution was allowed to cool down to room temperature and then a suspension of N-(3-acetyl-5-aminophenyl)methanesulfonamide (1 g) in acetic acid (8 mL) was gradually added with ice-cooling. The resulting mixture was allowed to stand at room temperature for 30 minutes and then stirred at 40° C. for 30 minutes to yield a dark red diazonium salt solution. The diazonium salt solution was gradually added to a solution of cuprous chloride (0.95 g) in concentrated hydrochloric acid (10 mL) at room temperature. After foaming was over, the reaction mixture was stirred at 80° C. for 30 minutes and then allowed to cool down to room temperature. Water (60 mL) was added and the mixture was extracted with ethyl acetate (100 mL). The ethyl acetate layer was washed with water (100 mL) three times and dried over anhydrous magnesium sulfate. The solvent was distilled off under reduced pressure. The residue was purified by silica gel column chromatography (98:2 chloroform/methanol) to yield N-(3-acetyl-5-chlorophenyl)methanesulfonamide (350 mg) as a light brown powder.

$^1$H-NMR (DMSO-d$_6$): δ(ppm) 7.72 (1H, m), 7.68 (1H, m), 7.55 (1H, m), 3.13 (3H, s), 2.61 (3H,s);

TLC (10:1 chloroform/methanol): R$_f$=0.60;

FAB-MS: m/z=249 (M+H)$^+$.

REFERENCE EXAMPLE 6

Synthesis of N-(3-acetyl-5-bromophenyl)methanesulfonamide

The procedure of Reference Example 4 was repeated using N-(3-acetyl-5-aminophenyl)methanesulfonamide (1 g) as the starting material except that cuprous bromide (1.5 g) and hydrobromic acid were used instead of cuprous chloride and concentrated hydrochloric acid. An after-treatment according to Reference Example 4 yielded N-(3-acetyl-5-bromophenyl)methanesulfonamide (350 mg) as a colorless crystal.

$^1$H-NMR (DMSO-d$_6$): δ(ppm) 10.21 (1H, brs), 7.83 (1H, m), 7,73 (1H, m), 7.60 (1H, m), 3.08 (3H, s), 2.57 (3H, s);

TLC (10:1 chloroform/methanol): R$_f$=0.86;

FAB-MS: m/z=293(M+H)$^+$.

REFERENCE EXAMPLE 7

Synthesis of N-(3-bromoacetyl-5-chlorophenyl)methanesulfonamide

N-(3-acetyl-5-chlorophenyl)methanesulfonamide (500 mg) was dissolved in dioxane (10 mL). The temperature was maintained at 50° C. and bromine (0.11 mL) was added. After stirring for 30 minutes, water (50 mL) was added to the mixture, and the mixture was extracted with ethyl acetate (50 mL). The ethyl acetate layer was washed with water (50 mL) twice and then dried over anhydrous magnesium sulfate. The solvent was distilled off under reduced pressure and the residue was purified by silica gel column chromatography (1:2 ethyl acetate/hexane) to yield N-(3-bromoacetyl-5-chlorophenyl)methanesulfonamide (600 mg) as a colorless crystal.

$^1$H-NMR (DMSO-d$_6$): δ(ppm) 10.29 (1H, brs), 7.80 (1H, m), 7.70 (1H, m), 7.50 (1H, m), 4.92 (2H,s), 3.80(3H,s);

TLC (1:1 n-hexane/ethyl acetate): R$_f$=0.85;

FAB-MS: m/z=328(M+H)$^+$.

REFERENCE EXAMPLE 8

Synthesis of N-(3-bromoacetyl-5-bromophenyl)methanesulfonamide

The procedure of Reference Example 6 was repeated using N-(3-acetyl-5-bromophenyl)methanesulfonamide (650 mg) as the starting material to yield N-(3-bromoacetyl-5-bromophenyl)methanesulfonamide (510 mg) as a light-brown powder.

$^1$H-NMR (DMSO-d$_6$): δ(ppm) 10.26 (1H, brs), 7.91 (1H, m), 7.75 (1H, m), 7.63 (1H, m), 4.91 (2H, s), 3.09 (3H, s);

TLC (1:1 n-hexane/ethyl acetate): R$_f$=0.75;

FAB-MS: m/z=372(M+H)$^{30}$.

REFERENCE EXAMPLE 9

Synthesis of 6-hydroxy-3-methyl-2-(pyridin-3-yl)-1H-indole (Step A) Synthesis of 5-methoxy-2-[(pyridin-3-yl)ethynyl]aniline In accordance with the process described in the literature (Wang et al., *J. Org. Chem.*, vol. 64, pp. 925-932, 1999), the title compound (397 mg) was obtained using 2-iodo-5-methoxyaniline (519 mg; synthesized according to the process described in the literature (Ma et al., *J. Org. Chem.*, vol. 66, pp. 4525-4542, 2001)), dichlorobis(triphenylphosphine)palladium(II)(60 mg), copper iodide(I)(20 mg), triethylamine (10 mL) and 3-ethynylpyridine (323 mg).

$^1$H-NMR (CDCl$_3$): δ(ppm) 3.79 (3H, s), 4.25-4.35 (2H, m), 6.27 (1H, d, J=2.7), 6.32 (1H, dd, J=8.7, 2.7), 7.24-7.30 (1H, m), 7.75-7.80 (1H, m), 8.52 (1H, dd, J=4.8, 1.5), 8.72-8.75 (1H, m);

TLC: R$_f$=0.10 (1:1 hexane/ethyl acetate).

(Step B) Synthesis of 6-methoxy-2-(pyridin-3-yl)-1H-indole

In accordance with the process described in the literature (Knochel et al., *Angew. Chem. Int. Ed.*, vol. 39, pp. 2488-2490, 2000), the title compound (337 mg) was obtained using the compound (397 mg; obtained in the step A of Reference Example 9), potassium-t-butoxide(418 mg) and 1-methyl-2-pyrrolidone (14 mL).

$^1$H-NMR (CDCl$_3$): δ(ppm) 3.88 (3H, s), 6.80-6.84 (2H, m), 6.91-6.93 (1H, m), 7.32-7.38 (1H, m), 7.52 (1H, d, J=8.4), 7.86-7.92 (1H, m), 8.24-8.34 (1H, brs), 8.50-8.54 (1H, m), 8.90-8.93 (1H, m);

TLC: R$_f$=0.10 (1:1 hexane/ethyl acetate).

(Step C) Synthesis of 6-methoxy-2-(pyridin-3-yl)-1H-indole-3-carboaldehyde

In accordance with the process described in the literature (Magnus et al., *J. Am. Chem. Soc.*, vol. 110, pp. 2242-2248, 1988) at the reaction temperature of 60° C., the title compound (573 mg) was obtained using the compound (557 mg; synthesized according to the process of the step B of Reference Example 9), phosphoryl chloride (350 μL) and DMF (5 mL).

$^1$H-NMR (DMSO-d$_6$): δ(ppm) 3.83 (3H, s), 6.91 (1H, dd, J=8.7, 2.4), 6.99 (1H, d, J=2.4), 7.62 (11H, dd, J=8.1, 4.5), 8.08 (1H, d, J=8.7), 8.17-8.22 (1H, m), 8.71-8.75 (1H, m), 8.95 (1H, d, J=2.1), 9.91 (1H, s), 12.25-12.47 (1H, brs).

(Step D) Synthesis of 6-methoxy-3-methyl-2-(pyridin-3-yl)-1H-indole

Lithium aluminium hydride (216 mg) was suspended in THF (20 mL), and the compound (573 mg; obtained in the step C of Reference Example 9) was gradually added at room temperature. The resulting mixture was heated to 40° C. and stirred at the same temperature for 5 minutes. The mixture was then cooled down to 0° C. Water (216 μL), an aqueous 15% sodium hydroxide solution (216 μL) and water (648 μL) were added in this order, and the resulting reaction mixture was filtered. The filtrate was concentrated under reduced pressure and the residue was purified by silica gel column chromatography (20:1 chloroform/methanol) to yield the title compound (506 mg).

$^1$H-NMR (CDCl$_3$): δ(ppm) 2.43 (3H, s), 3.86 (3H, s), 6.80-6.88 (2H, m), 7.37 (1H, dd, J=8.1, 4.8), 7.48 (1H, d, J=8.7), 7.82-7.86 (1H, m), 8.33-8.51 (1H, m), 8.53 (1H, d, J=4.8), 8.81-8.84 (1H,m);

TLC: R$_f$=0.57 (9:1 chloroform/methanol).

(Step E) Synthesis of 6-hydroxy-3-methyl-2-(pyridin-3-yl)-1H-indole

The compound (506 mg; obtained in the step D of Reference Example 9) was dissolved in methylene chloride (dehydrated, 10 mL), and boron tribromide (1 N solution in methylene chloride, 6.4 mL) was added dropwise under ice-cooling. The resulting mixture was allowed to warm to room temperature and stirred for 1 hour, followed by ice-cooling. Water was then added. The resulting mixture was extracted with chloroform, washed with saturated brine and dried over sodium sulfate. The solvent was distilled off under reduced pressure and the residue was then purified by silica gel chromatography (95:5-90:10 chloroform/methanol) to yield the title compound (456 mg).

$^1$H-NMR (CDCl$_3$): δ(ppm) 2.48 (3H, s), 6.66 (1H, dd, J=8.4, 1.8), 6.79 (1H, d, J=1.8), 7.34 (1H, d, J=8.4), 7.85 (1H, dd, J=8.1, 5.7), 8.43-8.48 (1H, m), 8.55 (1H, d, J=5.7), 8.89-8.92 (1H, m);

TLC: R$_f$=0.37 (9:1 chloroform/methanol).

REFERENCE EXAMPLE 10

Synthesis of ethyl 3-(6-hydroxy-3-methyl-1H-indol-2-yl)propionate (Step A) Synthesis of 6-methoxy-3-methyl-1H-indole-2-carboaldehyde In accordance with the process described in the step C of Reference Example 9, the title compound (4.60 g) was obtained as a crude product from 6-methoxy-3-methyl-1H-indole (3.89 g; synthesized according to the process described in the literature (Gan et al., *J. Org. Chem.*, vol. 62, pp. 9298-9304, 1997)), phosphoryl chloride (6.7 mL) and DMF (20 mL).

$^1$H-NMR (CDCl$_3$): δ(ppm) 2.60 (3H, s), 3.87 (3H, s), 6.76 (1H, d, J=2.1), 6.81 (1H, dd, J=8.7, 2.1), 7.56 (1H, d, J=8.7), 8.67-8.83 (1H, brs), 9.90 (1H, s);

TLC: R$_f$=0.39 (2:1 hexane/ethyl acetate).

(Step B) Synthesis of ethyl 3-(6-methoxy-3-methyl-1H-indol-2-yl)acrylate

In accordance with the process described in the literature (Kozikowski et al., *J. Med. Chem.*, vol. 36, pp. 2908-2920, 1993), the title compound (337 mg) was obtained using the compound (608 mg; obtained in the step A of Reference Example 10), (carbethoxymethylene)triphenylphosphorane (1.12 g) and toluene (30 mL).

$^1$H-NMR (CDCl$_3$): δ(ppm) 1.34 (3H, t, J=7.2), 2.38 (3H, s), 3.85 (3H, s), 4.28 (2H, q, J=7.2), 6.02 (1H, d, J=15.9), 6.74-6.79 (2H, m), 7.41-7.46 (1H, m), 7.77 (1H, d, J=15.9), 8.06-8.17 (11H, brs);

TLC: R$_f$=0.47 (2:1 hexane/ethyl acetate).

(Step C) Synthesis of ethyl 3-(6-methoxy-3-methyl-1H-indol-2-yl)propionate

The compound (337 mg; obtained in the step B of Reference Example 10) was dissolved in the mixture of methanol (6 mL) and THF (2 mL), and 10% palladium/carbon powder (177 mg) was added. The atmosphere in the system was replaced with a hydrogen atmosphere, followed by stirring at room temperature for 50 minutes. After the atmosphere in the system was replaced with an argon atmosphere, the catalyst was filtered and the solvent contained in the filtrate was distilled off under reduced pressure. The residue was then purified by silica gel column chromatography (1:1 hexane/ethyl acetate) to yield the title compound (333 mg).

$^1$H-NMR (CDCl$_3$): δ(ppm) 1.25 (3H, t, J=7.2), 2.20 (3H, s), 2.60-2.66 (2H, m), 2.96-3.02 (2H, m), 3.83 (3H, s), 4.16 (2H, q, J=7.2), 6.74 (1H, dd, J=8.7, 2.1), 6.79 (1H, d, J=2.1), 7.34 (1H, d, J=8.7), 8.22-8.27 (1H, brs);

TLC: R$_f$=0.47 (2:1 hexane/ethyl acetate).

(Step D) Synthesis of ethyl 3-(6-hydroxy-3-methyl-1H-indol-2-yl)propionate

In accordance with the process described in the step E of Reference Example 9, the title compound (239 mg) was obtained from the compound (330 mg; obtained in the step C of Reference Example 10), boron tribromide (1 N solution in methylene chloride, 3.0 mL) and methylene chloride (dehydrated, 6 mL).

$^1$H-NMR (CDCl$_3$): δ(Ppm) 1.25 (3H, t, J=7.2), 2.19 (3H, s), 2.59-2.66 (2H, m), 2.95-2.99 (2H, m), 4.16 (2H, q, J=7.2), 4.81-4.92 (1H, m), 6.64 (1H, dd, J=8.7, 2.1), 6.70-6.73 (1H, m), 7.29 (1H, d, J=8.7), 8.08-8.24 (1H, brs);

TLC: R$_f$=0.16 (2:1 hexane/ethyl acetate).

REFERENCE EXAMPLE 11

Synthesis of 6-hydroxy-3-methylindazole (Step A) Synthesis of 1-benzyl-3-methyl-6-methoxyindazole In accordance with the process described in the literature (S. Caron et al., *Synthesis*, No. 4, pp. 588-592, 1999), the title compound (4.58 g) was obtained from 2-acetyl-5-methoxyphenylmethanesulfonate (7.05 g), benzylhydrazine dihydrochloride (8.78 g) and acetic acid trihydrate (14.9 g).

$^1$H-NMR (CDCl$_3$): δ(ppm) 2.54 (3H, s), 3.80 (3H, s), 5.47 (2H, s), 6.58 (1H, d, J=1.9), 6.76 (1H, dd, J=8.8, 1.9), 7.16-7.32 (5H, m), 7.51 (1H, d, J=8.8).

(Step B) Synthesis of 1-benzyl-6-hydroxy-3-methylindazole

Pyridine hydrochloride was prepared by carefully mixing pyridine (100 mL) and concentrated hydrochloric acid (100 mL) in a flask equipped with a Liebig condenser and heating the resulting mixture at 180° C. with stirring to remove water. To the mixture, the compound (4.50 g; obtained in the step A of Reference Example 11) was added, followed by stirring at 180° C. for 2.5 hours. The reaction mixture was poured into ice water and the pH was adjusted to about 5 with an aqueous sodium hydroxide solution, followed by extraction with ethyl acetate. The organic layer was dried over anhydrous magnesium sulfate and the solvent was then distilled off under reduced pressure. After a mixed solution of chloroform and methanol (1:1) was added to the residue to form a homogeneous solution, the solvent was distilled off under reduced pressure. A mixed solvent of hexane and ether (1:1) was added to the residue to generate a crystal. The crystal thus collected by filtration was washed with a mixed solvent of hexane and ether (1:1) and then dried to give the title compound (2.20 g). In addition, the filtrate was concentrated and the residue was treated in the same manner to give the title compound (688 mg).

$^1$H-NMR (DMSO-$d_6$): δ(ppm) 2.40 (3H, s), 5.41 (1H, s), 6.62 (1H, dd, J=8.5, 1.9), 6.73 (1H, d, J=1.9), 7.15-7.33 (5H, m), 7.47 (1H, d, J=8.5), 9.59 (1H, s).

(Step C) Synthesis of 6-hydroxy-3-methylindazole

The compound (100 mg; obtained in the step B of Reference Example 11) was dissolved in a 0.1 N solution of hydrochloric acid in ethanol (5 mL) and 10% palladium/carbon powder (50 mg) was added. The resulting mixture was stirred under a hydrogen atmosphere at 40° C. for 5 hours. The catalyst was filtered off and the filtrate was concentrated to give the title compound (60 mg).

$^1$H-NMR (CD$_3$OD): δ(ppm) 2.37 (3H, s), 5.15 (2H, brs), 6.87 (1H, d, J=1.9), 6.99 (1H, dd, J=9.0, 1.9), 7.84 (11H, d, J=9.0).

EXAMPLE 1

Synthesis of ethyl (R)-6-[2-[2-(3-methylsulfonylamino)phenyl-2-hydroxyethylamino]ethoxy]-3-methyl-i 1H-indole-2-carboxylate hydrochloride (Step A) Synthesis of ethyl 3-methyl-6-hydroxy-1H-indole-2-carboxylate Ethyl 3-methyl-6-methoxy-1H-indole-2-carboxylate (1.00 g; synthesized according to the disclosures in the literature (Gan et al., *J. Org. Chem.*, vol. 62, pp. 9298-9304, 1997)) was dissolved in methylene chloride (dehydrated, 13 mL), and boron tribromide (1 M/methylene chloride, 17.2 mL) was added dropwise under ice-cooling. The resulting mixture was allowed to warm to room temperature and stirred for 40 minutes. The reaction solution was then cooled with ice, followed by addition of water. The resulting mixture was extracted with chloroform, washed with saturated brine and dried over sodium sulfate. After the solvent was distilled off under reduced pressure, the residue was purified by silica gel chromatography (3:1-2:1 hexane/ethyl acetate) to yield the title compound (480 mg).

$^1$H-NMR (CDCl$_3$): δ(ppm) 1.42 (3H, t, J=6.9), 2.57 (3H, s), 4.39 (2H, q, J=6.9), 4.86 (1H, s), 6.71 (1H, dd, J=8.7, 2.1), 6.77 (1H, d, J=2.1), 7.51 (1H, d, J=8.7), 8.48 (1H brs).

(Step B) Synthesis of (R)-[3-[2-[N-benzyl-N-[2-(2-ethoxycarbonyl-3-methyl-1H-indol-6-yloxy)ethyl]amino]-1-triethylsilyloxy]ethylphenyl](methylsulfonyl)benzylamine The compound (87 mg; obtained in the above step A), the compound of Reference Example 1 (262 mg) and 1,1'-azobis(N,N-dimethylformamide)(136 mg) were dissolved in THF (5 mL). After the resulting solution was cooled to 0° C., tributyl phosphine (196 μL) was added dropwise, followed by stirring for 10 minutes. The resulting mixture was then allowed to warm to room temperature and stirred overnight. To the reaction mixture, water (10 mL) was added. The resulting mixture was extracted with ethyl acetate three times and dried over magnesium sulfate. After the solvent was distilled off under reduced pressure, the residue was purified by silica gel chromatography (5:1-2:1 hexane/ethyl acetate) to yield the title compound (193 mg) as a light yellow oil.

$^1$H-NMR (CDCl$_3$): δ(ppm) 0.38-0.48 (6H, m), 0.81 (9H, t, J=7.8), 1.43 (3H, t, J=7.2), 2.56 (3H, s), 2.68-2.91 (4H, m), 2.87 (3H, s), 3.65-3.82 (4H, m), 4.40 (3H, q, J=7.2), 4.59 (1H, t, J=5.7), 4.77 (1H, d, J=14.7), 4.86 (1H, d, J=14.7), 6.53 (1H, d, J=2.1), 6.69 (1H, dd, J=5.7, 2.1), 7.10-7.30 (14H, m), 7.47 (1H, d, J=5.7), 8.66-8.72 (1H, brs).

(Step C) Synthesis of (R)-2-[N'-benzyl-N'-[2-(2-ethoxycarbonyl-3-methyl-1H-indol-6-yloxy)ethyl]amino]-1-[3-(N-benzyl-N-methylsulfonylamino)phenyl]ethanol The compound (193 mg; obtained in the above step B) was dissolved in THF (5 mL). Acetic acid (115 μL) and tetra-n-butylammonium fluoride (1.0 M/THF solution, 2.0 mL) were added and the resulting mixture was stirred at room temperature for 2 hours. To the reaction mixture, a saturated aqueous sodium hydrogencarbonate solution was added. The resulting mixture was extracted with ethyl acetate three times and dried over magnesium sulfate. After the solvent was distilled off under reduced pressure, the residue was purified by silica gel chromatography (3:1-2:3 hexane/ethyl acetate) to yield the title compound (161 mg).

$^1$H-NMR (CDCl$_3$): δ(ppm) 1.42 (3H, t, J=7.2), 2.575 (3H, s), 2.582 (1H, t, J=10.2), 2.80 (1H, dd, J=10.2, 3.6), 2.89 (3H, s), 2.92-3.02 (1H, m), 3.06-3.17 (1H, m), 3.68 (1H, d, J=13.5), 3.95 (1H, d, J=13.5), 4.02-4.09 (2H, m), 4.40 (2H, q, J=7.2), 4.66 (1H, dd, J=10.2, 3.6), 4.80 (2H, s), 6.75 (1H, d, J=2.1), 6.81 (1H, dd, J=9.0, 2.1), 7.09-7.35 (14H, m), 7.52 (1H, d, J=9.0), 8.59-8.66 (1H, brs).

(Step D) Synthesis of ethyl (R)-6-[2-[2-(3-methylsulfonylamino)phenyl-2-hydroxyethylamino]ethoxy]-3-methyl-1H-indole-2-carboxylate hydrochloride The compound (161 mg; obtained in the above step C) was dissolved in ethanol (12 mL) and THF (6 mL). To the resulting solution, 20% palladium hydroxide/carbon powder (50% moisture, 103 mg) was added. After the atmosphere in the system was replaced with a hydrogen atmosphere, the mixture was stirred at 60° C. for 80 minutes. The atmosphere in the system was replaced with an argon atmosphere and chloroform (5 mL) was then added. After the resulting mixture was filtered and 0.1 N hydrochloric acid in ethanol (7 mL) was added to the filtrate, the solvent was distilled off under reduced pressure. Chloroform was added to the residue. The deposited solid was then collected by filtration and dried to yield the title compound (96 mg).

$^1$H-NHR (DMSO-$d_6$): δ(ppm) 1.35 (3H, t, J=6.9), 3.00 (3H, s), 3.01-3.13 (1H, m), 3.22-3.34 (1H, m), 3.41-3.50 (2H, m), 4.27-4.37 (4H, m), 4.94-5.02 (1H, m), 6.24 (1H, d, J=3.3), 6.79 (1H, dd, J=8.7, 2.1), 6.88 (1H, d, J=2.1), 7.10-7.19 (2H, m), 7.28-7.33 (1H, m), 7.36 (1H, t, J=7.5), 7.57 (1H, d, J=8.7), 8.78-9.15 (2H, m), 9.85 (1H, s), 11.33 (1H, s).

TLC: $R_f$=0.33 (free form)(9:1 chloroform/methanol).

EXAMPLE 2

Synthesis of (R)-6-[2-[2-(3-methylsulfonylamino) phenyl-2-hydroxyethylamino]ethoxy]-3-methyl-i 1H-indole-2-carboxylic acid hydrochloride The compound (47 mg; obtained in Example 1) was dissolved in methanol (10 mL). An aqueous sodium hydroxide solution (2.0 M, 450 μL) was added and the resulting mixture was stirred at a temperature of 50 to 55° C. for 4 hours. The reaction mixture was cooled down to room temperature and 0.1 N hydrochloric acid in ethanol (8 mL) was added. The solvent was distilled off under reduced pressure and water (5 mL) was added to the residue. The solid was collected by filtration and dried to give the title compound (28 mg).

$^1$H-NMR (DMSO-$d_6$): δ(ppm) 3.00 (3H, s), 3.07 (1H, t, J=12.9), 3.22-3.32 (1H, m), 3.41-3.50 (2H, m), 4.26-4.36 (2H, m), 4.92-5.02 (1H, m), 6.21-6.27 (1H, m), 6.79 (1H, m), 6.79 (1H, dd, J=8.7, 2.4), 6.87 (1H, d, J=2.4), 7.10-7.19 (2H, m), 7.28-7.34 (1H, m), 7.36 (1H, t, J=7.8), 7.58 (1H, d, J=8.7), 8.74-9.10 (2H, m), 9.85 (1H, s), 11.39 (1H, s);

TLC: $R_f$=0.33 (free form)(9:1 chloroform/methanol).

EXAMPLE 3

Synthesis of ethyl (R)-1-methyl-6-[2-[2-(3-methylsulfonylamino)phenyl-2-hydroxyethylamino] ethoxy]-3-methyl-i 1H-indole-2-carboxylate hydrochloride (Step A) Synthesis of (R)-2-[N'-benzyl-N'-[2-(2-ethoxycarbonyl-3-methyl-1-methylindol-6-yloxy) ethyl]amino]-1-[3-(N-benzyl-N-methylsulfonylamino)phenyl]ethanol The compound (102 mg; obtained in the step A of Example 1 set forth above), the compound (314 mg; obtained in Reference Example 1) and 1,1'-azobis(N,N-dimethylformamide)(162 mg) were dissolved in THF (5 mL). After the resulting solution was cooled to 0° C., tributyl phosphine (230 μL) was added dropwise, followed by stirring for 10 minutes. The resulting mixture was then allowed to warm to room temperature and stirred overnight. To the reaction mixture, water (10 mL) was added. The mixture was extracted with ethyl acetate three times and dried over anhydrous magnesium sulfate. After the solvent was distilled off under reduced pressure, the residue was purified by silica gel chromatography (5:1-3:1 hexane/ethyl acetate). The residue was dissolved in THF (2 mL) and sodium hydride (60% in paraffin, 45 mg) was added, followed by stirring at room temperature for 10 minutes. Methyl iodide (58 μL) was added to the reaction mixture and the mixture was stirred at room temperature for 20 minutes. The mixture was neutralized with an aqueous hydrochloric acid solution, and then extracted with ethyl acetate four times and dried over magnesium sulfate. The solvent was distilled off under reduced pressure and the residue was then purified by silica gel chromatography (4:1-2:1 hexane/ethyl acetate). The thus purified residue was dissolved in THF (1 mL) after the solvent was distilled off. Acetic acid (30 μL) and tetra-n-butylammonium fluoride (1.0 M/THF solution, 0.5 mL) were added and the resulting mixture was stirred at room temperature for 1 hour. The reaction mixture was neutralized with an aqueous sodium hydroxide solution, and then extracted with ethyl acetate three times and dried over magnesium sulfate. After the solvent was distilled off under reduced pressure, the residue was purified by silica gel chromatography (2:1-2:3 hexane/ethyl acetate) to yield the title compound (73 mg).

$^1$H-NMR (CDCl$_3$): δ(ppm) 1.43 (3H, t, J=7.2), 2.56 (3H, s), 2.58 (1H, dd, J=12.9, 10.2), 2.80 (1H, dd, J=12.9, 3.6), 2.88 (3H, s), 2.99 (1H, dt, J=14.1, 5.1), 3.15 (1H, dt, J=14.1, 5.4), 3.70 (1H, d, J=13.5), 3.94 (3H, s), 3.97 (1H, d, J=13.5), 4.08-4.14 (2H, m), 4.39 (2H, q, J=7.2), 4.66 (1H, dd, J=10.2, 3.6), 4.80 (2H, s), 6.68 (1H, d, J=2.1), 6.82 (1H, dd, J=9.0, 2.1), 7.12 (1H, dt, J=7.5, 2.1), 7.17-7.36 (13H, m), 7.53 (1H, d, J=9.0).

(Step B) Synthesis of ethyl (R)-1-methyl-6-[2-[2-(3-methylsulfonylamino)phenyl-2-hydroxyethylamino]ethoxy]-3-methyl-1H-indole-2-carboxylate hydrochloride The compound (73 mg; obtained in the above step A) was dissolved in ethanol (10 mL) and THF (5 mL). To the resulting solution, 20% palladium hydroxide/carbon powder (50% moisture, 72 mg) was added. After the atmosphere in the system was replaced with a hydrogen atmosphere, the mixture was stirred at 60° C. for 2 hours. The atmosphere in the system was replaced with an argon atmosphere and chloroform (5 mL) was then added. After the resulting mixture was filtered and 0.1 N hydrochloric acid in ethanol (7 mL) was added to the filtrate, the solvent was distilled off under reduced pressure. A small amount of chloroform and diethyl ether was added to the residue. The deposited solid was then collected by filtration and dried to yield the title compound (42 mg).

$^1$H-NMR (DMSO-$d_6$): δ(ppm) 1.35 (3H, t, J=7.2), 2.98-3.16 (1H, m), 3.00 (3H, s), 3.20-3.32 (1H, m), 3.39-3.54 (2H, m), 3.92 (3H, s), 4.32 (2H, q, J=7.2), 4.36-4.45 (2H, m), 4.96-5.05 (1H, m), 6.26 (1H, d, J=3.9), 6.83 (1H, dd, J=8.7, 2.1), 7.09 (1H, d, J=2.1), 7.10-7.19 (2H, m), 7.29-7.33 (1H, m), 7.36 (1H, t, J=7.5), 7.61 (1H, d, J=8.7), 8.87-9.07 (1H, brs), 9.10-9.28 (1H, brs), 9.85 (1H, s);

TLC: $R_f$=0.37 (free form)(9:1 chloroform/methanol).

EXAMPLE 4

Synthesis of (R)-1-methyl-6-[2-[2-(3-methylsulfonylamino)phenyl-2-hydroxyethylamino]ethoxy]-3-methyl-1H-indole-2-carboxylic acid hydrochloride In accordance with the process described in Example 2, the title compound (9.6 mg) was obtained from the compound of Example 3.

According to the processes described in Examples 1 to 4, the compounds (Examples 5 to 83) listed in Table 1 were synthesized. Among the compounds of Table 1, the compounds of Examples 13, 14, 16, 20, 24 and 72 to 83 were analyzed by liquid chromatograph/mass spectrometry (LC-MS). The results obtained from the analyses confirm that the objective compounds of the Examples were produced.

TABLE 1

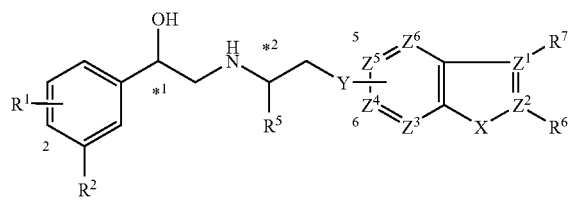

(wherein $Z^2$ to $Z^6$ represent a carbon atom)

| Ex. | $R^1$ | $R^2$ | $R^5$ | Y | X | $R^6$ | $R^7$ | $Z^1$ |
|---|---|---|---|---|---|---|---|---|
| 5 | H | NHSO$_2$Me | H | 6-O | NH | Me | CO$_2$Et | C |
| 6 | H | NHSO$_2$Me | H | 6-O | NH | Me | CO$_2$H | C |
| 7 | H | NHSO$_2$Me | H | 6-O | NH | Me | CH$_2$OH | C |
| 8 | H | NHSO$_2$Me | H | 6-O | NH | Me | CH$_2$NMe$_2$ | C |
| 9 | H | NHSO$_2$Me | H | 6-O | NH | Me | CH$_2$CO$_2$Et | C |
| 10 | H | NHSO$_2$Me | H | 6-O | NH | Me | CH$_2$CO$_2$H | C |
| 11 | H | NHSO$_2$Me | H | 6-O | NH | Me | CH=CHCO$_2$Et | C |
| 12 | H | NHSO$_2$Me | H | 6-O | NH | Me | CH=CHCO$_2$H | C |
| 13 | H | NHSO$_2$Me | H | 6-O | NH | Me | CH$_2$CH$_2$CO$_2$Et | C |
| 14 | H | NHSO$_2$Me | H | 6-O | NH | Me | CH$_2$CH$_2$CO$_2$H | C |
| 15 | H | NHSO$_2$Me | H | 6-O | NH | Me | CH$_2$CH$_2$NH$_2$ | C |
| 16 | H | NHSO$_2$Me | H | 6-O | NH | Me | CH$_2$CH$_2$NMe$_2$ | C |
| 17 | H | NHSO$_2$Me | H | 6-O | NH | Me | COCH$_3$ | C |
| 18 | H | NHSO$_2$Me | H | 6-O | NH | Et | CH$_2$CO$_2$Et | C |
| 19 | H | NHSO$_2$Me | H | 6-O | NH | Et | CH$_2$CO$_2$H | C |
| 20 | H | NHSO$_2$Me | H | 6-O | NH | Et | CH$_2$CH$_2$CO$_2$Et | C |
| 21 | H | NHSO$_2$Me | H | 6-O | NH | Et | CH$_2$CH$_2$CO$_2$H | C |
| 22 | H | NHSO$_2$Me | H | 6-O | NH | Ph | CH$_2$CO$_2$Et | C |
| 23 | H | NHSO$_2$Me | H | 6-O | NH | Ph | CH$_2$CO$_2$H | C |
| 24 | H | NHSO$_2$Me | H | 6-O | NH | Ph | CH$_2$CH$_2$CO$_2$H | C |
| 25 | 2-Cl | NHSO$_2$Me | H | 6-O | NH | Me | CH$_2$CO$_2$Et | C |
| 26 | 2-Cl | NHSO$_2$Me | H | 6-O | NH | Me | CH$_2$CO$_2$H | C |
| 27 | 2-F | NHSO$_2$Me | H | 6-O | NH | Me | CH$_2$CO$_2$Et | C |
| 28 | 2-F | NHSO$_2$Me | H | 6-O | NH | Me | CH$_2$CO$_2$H | C |
| 29 | 2-OH | SO$_2$NHMe | H | 6-O | NH | Me | CH$_2$CO$_2$Et | C |
| 30 | H | NHSO$_2$Me | H | 6-O | NH | CH$_2$CH$_2$OMe | CH$_2$CO$_2$Et | C |
| 31 | H | NHSO$_2$Me | H | 6-O | NH | CH$_2$CH$_2$OMe | CH$_2$CH$_2$CO$_2$H | C |
| 32 | H | RHSO$_2$Me | H | 6-O | NH | CH$_2$CH$_2$OMe | Me | C |
| 33 | H | NHSO$_2$Me | H | 6-O | NH | CH$_2$CH$_2$OMe | Et | C |
| 34 | H | NHSO$_2$Me | H | 6-NH | NH | CO$_2$Et | Me | C |
| 35 | H | NHSO$_2$Me | H | 6-NH | NH | CO$_2$H | Me | C |
| 36 | 2-Cl | NHSO$_2$Me | H | 6-O | NH | CH$_2$CO$_2$Et | Me | C |
| 37 | 2-F | NHSO$_2$Me | H | 6-O | NH | CH$_2$CO$_2$Et | Me | C |
| 38 | 2-F | NHSO$_2$Me | (R)—Me | 6-O | NH | CO$_2$Et | Me | C |
| 39 | H | NHSO$_2$Me | H | 6-O | O | CO$_2$Et | Me | C |
| 40 | H | NHSO$_2$Me | H | 6-O | O | CO$_2$H | Me | C |
| 41 | H | NHSO$_2$Me | H | 6-O | O | CH$_2$CO$_2$Et | Me | C |
| 42 | H | NHSO$_2$Me | H | 6-O | O | CH$_2$CO$_2$H | Me | C |
| 43 | H | NHSO$_2$Me | H | 6-O | O | Me | CH$_2$CO$_2$Et | C |
| 44 | H | NHSO$_2$Me | H | 6-O | O | Me | CH$_2$CO$_2$H | C |
| 45 | H | NHSO$_2$Me | H | 6-O | O | Me | CH$_2$CH$_2$CO$_2$Et | C |
| 46 | H | NHSO$_2$Me | H | 6-O | O | Me | CH$_2$CH$_2$CO$_2$H | C |
| 47 | H | NHSO$_2$Me | H | 6-O | O | Ph | CH$_2$CO$_2$Et | C |
| 48 | H | NHSO$_2$Me | H | 6-O | O | Ph | CH$_2$CO$_2$H | C |
| 49 | H | NHSO$_2$Me | H | 6-O | O | Ph | CH$_2$CH$_2$CO$_2$Et | C |
| 50 | H | NHSO$_2$Me | H | 6-O | O | Ph | CH$_2$CH$_2$CO$_2$H | C |
| 51 | H | NHSO$_2$Me | H | 6-O | S | Ph | CH$_2$CO$_2$Et | C |
| 52 | H | NHSO$_2$Me | H | 6-O | S | Ph | CH$_2$CH$_2$CO$_2$Et | C |
| 53 | H | NHSO$_2$Me | H | 6-O | O | CON(CH$_2$)$_4$ | H | C |
| 54 | H | NHSO$_2$Me | H | 6-O | O | Isoxazol-3-yl | H | C |
| 55 | H | NHSO$_2$Me | H | 5-O | NH | CO$_2$Et | Me | C |

| Ex. | $R^1$ | $R^2$ | $R^5$ | Y | X | $R^6$ | $R^7$ | $Z^2$ |
|---|---|---|---|---|---|---|---|---|
| 56 | H | NHSO$_2$Me | H | 6-O | NMe | CO$_2$Et | H | C |
| 57 | H | NHSO$_2$Me | H | 6-O | NMe | CO$_2$H | H | C |
| 58 | H | NHSO$_2$Me | H | 6-O | NCH$_2$Ph | CO$_2$H | H | C |
| 59 | H | NHSO$_2$Me | H | 6-O | NCH$_2$Ph | CH$_2$CO$_2$H | H | C |
| 60 | H | NHSO$_2$Me | H | 6-O | NCH$_2$Ph | CH$_2$CH$_2$CO$_2$H | H | C |
| 61 | H | NHSO$_2$Me | H | 6-O | NCH$_2$Ph | CH$_2$CH$_2$NMe$_2$ | H | C |
| 62 | H | NHSO$_2$Me | H | 6-O | NCH$_2$Ph—NHMs-m | CO$_2$H | H | C |
| 63 | H | NHSO$_2$Me | H | 6-O | NCH$_2$Ph—NHMs-m | CH$_2$CO$_2$H | H | C |
| 64 | H | NHSO$_2$Me | H | 6-O | NCH$_2$Ph—NHMs-m | CH$_2$CH$_2$CO$_2$H | H | C |

TABLE 1-continued

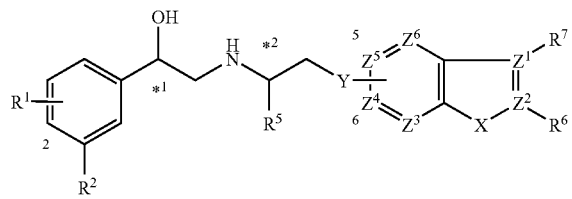

(wherein $Z^2$ to $Z^6$ represent a carbon atom)

| | | | | | | | | |
|---|---|---|---|---|---|---|---|---|
| 65 | H | NHSO$_2$Me | H | 6-O | NCH$_2$Ph—NHMs-m | CH$_2$CH$_2$NMe$_2$ | H | C |
| 66 | H | NHSO$_2$Me | H | 6-O | NCH$_2$Ph—NHMs-p | CO$_2$H | H | C |
| 67 | H | NHSO$_2$Me | H | 6-O | NCH$_2$Ph—NHMs-p | CH$_2$CO$_2$H | H | C |
| 68 | H | NHSO$_2$Me | H | 6-O | NCH$_2$Ph—NHMs-p | CH$_2$CH$_2$CO$_2$H | H | C |
| 69 | H | NHSO$_2$Me | H | 6-O | NCH$_2$Ph—NHMs-p | CH$_2$CH$_2$NMe$_2$ | H | C |
| 70 | H | NHSO$_2$Me | H | 6-O | NH | CF$_3$ | CF$_3$ | C |
| 71 | H | NHSO$_2$Me | H | 6-O | NH | CO$_2$H | — | N |
| 72 | H | NHSO$_2$Me | H | 6-O | NH | 3-pyridyl | Me | C |
| 73 | H | NHSO$_2$Me | H | 6-O | NH | 3-pyridyl | Et | C |
| 74 | H | NHSO$_2$Me | H | 6-O | NH | 4-pyridyl | CH$_3$ | C |
| 75 | H | NHSO$_2$Me | H | 6-O | NH | N-Boc-3-piperidinyl | Me | C |
| 76 | H | NHSO$_2$Me | H | 6-O | NH | 3-piperidinyl | Me | C |
| 77 | H | NHSO$_2$Me | H | 6-O | NH | Me | CH$_2$CH$_2$NHAc | C |
| 78 | H | NHSO$_2$Me | H | 6-O | NH | Ph | CH$_2$CH$_2$CO$_2$Et | C |
| 79 | 2-F | NHSO$_2$Me | H | 6-O | NH | 3-pyridyl | Me | C |
| 80 | 2-F | NHSO$_2$Me | H | 6-O | NH | CH$_2$CH$_2$CO$_2$Et | Me | C |
| 81 | H | NHSO$_2$Me | H | 6-O | NH | CH$_2$CH$_2$CONMe$_2$ | Me | C |
| 82 | H | NHSO$_2$Me | H | 6-O | NH | CH$_2$CH$_2$CO$_2$Et | Me | C |
| 83 | H | NHSO$_2$Me | H | 6-O | NH | CH$_2$CO$_2$Et | Me | C |

Examples 84 and 85

Synthesis of (R)-N-[3-[2-[2-(3-methylindazol-6-yloxy)ethylamino]-1-hydroxyethyl]phenyl]methanesulfonamide hydrochloride (Example 84) Synthesis of (R)-N-[3-[2-[2-(1-benzyl-3-methylindazol-6-yloxy)ethylamino]-1-hydroxyethyl]phenyl]methanesulfonamide hydrochloride (Example 85)

(Step A) Synthesis of (R)—N-benzyl-N-[3-[2-[N'-benzyl-2-(1-benzyl-3-methylindazol-6-yloxy)ethylamino]-1-triethylsilyloxyethyl]phenyl]methanesulfonamide In accordance with the process described in the step B of Example 1, the title compound (1.58 g) was obtained from the compound (1.27 g; described in Reference Example 1), the compound (530 mg; obtained in the step B of Reference Example 11), 1,1'-azobis(N,N-dimethylformamide)(860 mg) and triphenylphosphine (1.31 g).

$^1$H-NMR (CDCl$_3$): δ(ppm) 0.37-0.46 (6H, m), 0.80 (9H, t, J=7.9), 2.52 (3H, 2.87 (2H, m), 2.80 (3H, s), 3.64-3.70 (4H, m), 4.56 (1H, t, J=6.0), 4.72-4.83 (2H, m), 5.44 (2H, m), 6.42 (1H, d, J=2.2), 7.67 (1H, dd, J=8.8, 2.2), 7.02-7.35 (19H, m), 7.47 (1H, d, J=8.8).

(Step B) Synthesis of (R)—N-benzyl-N-[3-[2-[N'-benzyl-2-(1-benzyl-3-methylindazol-6-yloxy)ethylamino]-1-hydroxyethyl]phenyl]methanesulfonamide In accordance with the process described in the step C of Example 1, the title compound (1.05 g) was obtained from the compound (1.58 g; obtained in the above step A).

$^1$H-NMR (CDCl$_3$): δ(ppm) 2.51-2.58 (1H, m), 2.54 (3H, s), 2.74-2.80 (1H, m), 2.88 (3H, s), 2.87-3.14 (2H, m), 3.66 (1H, d, J=13.7), 3.92 (1H, d, J=13.7), 3.98 (2H, t, J=5.2), 4.63 (1H, dd, J=9.8, 3.0), 4.80 (2H, s), 5.46 (2H, s), 6.55 (1H, d, J=1.9), 6.78 (1H, dd, J=8.5, 1.9), 7.10-7.35 (15H, m), 7.52 (1H, d, J=8.5).

(Step C) Syntheses of (R)-N-[3-[2-[2-(3-methylindazol-6-yloxy)ethylamino]-1-hydroxyethyl]phenyl]methanesulfonamide hydrochloride and (R)-N-[3-[2-[2-(1-benzyl -3-methylindazol-6-yloxy)ethylamino]-1-hydroxyethyl]phenyl]methanesulfonamide hydrochloride The compound (740 mg; obtained in the above step B) was dissolved in a mixed solvent of THF (5 mL) and methanol (5 mL). To the resulting solution, 20% palladium hydroxide/carbon powder (50% moisture, 186 mg) was added. After the atmosphere in the system was replaced with a hydrogen atmosphere, the mixture was stirred at 50° C. for 6 hours. The catalyst was separated by filtration and the filtrate was concentrated under reduced pressure. The compound of Example 85 was obtained by purifying 50 mg aliquot of the residue. The remainder of the residue was dissolved in a 0.1 N hydrochloric acid solution in ethanol (13 mL) and 20% palladium hydroxide/carbon powder (50% moisture, 203 mg) was added. After the atmosphere in the system was replaced with a hydrogen atmosphere, the mixture was stirred at 50° C. for 1 hour. After the generated precipitate was dissolved by adding a small amount of concentrated ammonia water, the catalyst was separated by filtration and the filtrate was concentrated under reduced pressure. The residue was dissolved in ethanol and a 0.1 N hydrochloric acid solution in ethanol was added. The generated crystal was filtered, washed with ether and then dried to yield the compound (274 mg) of Example 84.

(Example 84): (R)-N-[3-[2-[2-(3-methylindazol-6-yloxy)ethylamino]-1-hydroxyethyl]phenyl]methanesulfonamide hydrochloride; $^1$H-NMR (DMSO-d$_6$):

δ(ppm) 2.45 (3H, s), 3.00 (3H, s), 3.02-3.32 (2H, m), 3.42-3.50 (2H, m), 4.32-4.38 (2H, m), 4.79 (2H, br), 4.98-5.02 (1H, m), 6.78 (1H, dd, J=8.8, 2.2), 6.91 (1H, d, J=2.2), 7.12-7.17 (2H, m), 7.30-7.38 (2H, m), 7.61 (1H, d, J=8.8), 8.99 (1H, br), 9.26 (1H, br), 9.85 (1H, s);

(Example 85): (R)-N-[3-[2-[2-(1-benzyl-3-methylindazol-6-yloxy)ethylamino]-1-hydroxyethyl]phenyl]methanesulfonamide hydrochloride; $^1$H-NMR (DMSO-d$_6$):

δ(ppm) 2.43 (3H, s), 3.00 (3H, s), 3.01-3.49 (4H, m), 4.34-4.39 (2H, m), 4.96-5.02 (1H, m), 5.52 (2H, s), 6.79 (1H, dd, J=8.8, 1.9), 7.11-7.38 (11H, m), 7.61 (1H, d, J=8.8), 8.96 (1H, br), 9.13 (1H, br), 9.85 (1H, s).

According to the processes described in Examples 84 and 85, the compounds (Examples 86 to 90) listed in Table 2 were synthesized. These compounds were analyzed by liquid chromatograph/mass spectrometry (LC-MS). The results obtained from the analyses showed that the objective compounds of said Examples were produced.

TABLE 2

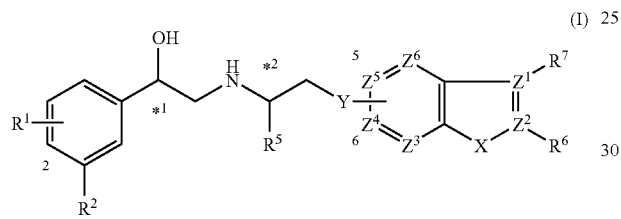

(I)

(wherein $Z^1$ and $Z^3$ to $Z^6$ represent a carbon atom; $Z^2$ represents a nitrogen atom; and $R^6$ is absent)

| Ex. | $R^1$ | $R^2$ | $R^5$ | Y | X | $R^7$ |
|---|---|---|---|---|---|---|
| 86 | H | NHSO$_2$Me | H | 6-O | NH | OMe |
| 87 | 4-F | NHSO$_2$Me | H | 6-O | NH | Me |
| 88 | 2-Cl | NHSO$_2$Me | H | 6-O | NH | Me |
| 89 | OH | SO$_2$NHMe | H | 6-O | NH | Me |
| 90 | H | NHSO$_2$Me | (R)—Me | 6-O | NH | Me |

TEST EXAMPLE 1

Human β3-Agonist Activities

Human β3-agonist activities were determined using CHO (Chinese hamster ovary) cells transfected with pcDNA3 (mfd. by Invitrogen) to which human β3 gene had been inserted. Human β3 fragment was first obtained from human adipose tissue cDNA (mfd. by Clonetech) by PCR using the primer of β3 (Krief, et al., *J. Clin. Invest.*, vol. 91, pp. 344-349 (1993)). The human β3 fragment thus obtained was used as a probe to obtain the full length human β3 gene from a human genomic library (mfd. by Clonetech). The above cells were cultured in a Ham F-12 medium supplemented with 10% fetal bovine serum, 400 μg/mL geneticin (Gibco BRL), 100 U/mL penicillin and 100 μg/nm streptomycin. After placing these cells (5×10$^5$) into a 6-well plate and culturing them for 24 hours, they were allowed to stand on a serum-free Ham F-12 medium for 2 hours. The compound was first dissolved in DMSO, repeatedly diluted by ten times with Ham F-12 supplemented with 1 mM isobutylmethylxanthine and 1 mM ascorbic acid to a final concentration of from 10$^{-5}$ to 10$^{-12}$ M, and then added to the cells. After the cells were cultured for 30 minutes, the medium was removed, followed by addition of 0.5 mL of 1 N NaOH. The medium was allowed to stand for 20 minutes and then 0.5 mL of 1 N acetic acid was added to the medium. The medium was stirred and then centrifuged, followed by quantitating cAMP with cAMP EIA kit (mfd. by Cayman). With respect to several compounds among the compounds described in Examples, their EC$_{50}$ values are indicated in Table 3. Isoproterenol was purchased from RBI (Research Biochemicals International). It has been found that the compounds of the present invention have human β3-agonist activities.

TABLE 3

| Compound | EC$_{50}$(nM) | Intrinsic activity* % |
|---|---|---|
| Example 1 | 15 | 97 |
| Example 2 | 18 | 124 |
| Example 13 | 23 | 38 |
| Example 20 | 32 | 55 |
| Example 72 | 2.8 | 105 |
| Example 73 | 3.5 | 75 |
| Example 74 | 3.9 | 71 |
| Example 75 | 4.4 | 79 |
| Example 76 | 21 | 76 |
| Example 78 | 43 | 71 |
| Example 79 | 3.4 | 65 |
| Example 80 | 2.8 | 63 |
| Example 81 | 2.8 | 77 |
| Example 82 | 1.4 | 81 |
| Example 84 | 12 | 81 |
| Example 86 | 26 | 64 |
| Example 87 | 24 | 56 |
| Example 88 | 4.7 | 52 |
| Example 89 | 11 | 80 |

*Relative activities (%) as compared with isoproterenol.

TEST EXAMPLE 2

Action on the Heart

The heart was excised from a male guinea pig weighing 180-250 g to prepare a specimen of the right atrium. The specimen was set in an organ bath filled with a Krebs solution which had been aerated with a mixed gas of 5%CO$_2$/95%O$_2$. The automaticity was determined using a isometric transducer (NIHON KOHDEN TB-611T) connected to a polygraph (NIHON KOHDEN MR-6000). The present compounds described in the Examples have a higher ED$_{50}$ value than that of β3. Therefore, these compounds were expected to have selective actions and hardly induce an increase of the heart rate, that is, to entail little side effects.

TEST EXAMPLE 3

Pharmacological Effect on a Transgenic Mouse Expressing Human β3

A transgenic mouse expressing human β3 was prepared according to the method reported by Hogan et al. (A Laboratory Manual, 2nd Ed., Cold Spring Harbor Laboratory Press, Cold Spring Harbor, N.Y.) by linking mouse β3 promoter to upstream of human β3 gene used in Test Example 1. The mouse expressed human β3 gene in an organ which expresses mouse β3.

After fasting for four hours, the transgenic mouse was orally dosed with a compound of the present invention dissolved in 10% hydroxypropyl-β-cyclodextrin (Aldrich) at a dose of 0.1 mL/10 g body-weight. After 0 minute, 30 minutes, 1 hour and 2 hours, blood samples are collected from venous plexus of the eyeground. A blood glucose level was determined by measuring the serum glucose concentration in the sample using Glucose Test B Test Wako (Wako Pure Chemical Industries). A free fatty acid level was measured using NEFA HA Test Wako (Wako Pure Chemical Industries). It was found that compounds of the present invention exhibit hypoglycemic activity and lipolytic activity while increasing the blood free fatty acid concentration.

The thermogenesis was measured with an OXYMAX System (Columbus) according to the method reported by Largis et al. (Drug Development Research, vol. 32, pp. 69-76 (1994)). The measurement of thermogenesis carried out, after the oral administration of a compound of the present invention showed the compounds of the present invention to posses thermogenesis increasing activities.

The results set forth above demonstrate that compounds of the present invention are effective in treating obesity and diabetes.

TEST EXAMPLE 4

Therapeutic Effect for Urinary Incontinence

The contractive power of human urinary bladder detrusor was determined according to the method reported by Takeda M. et al. (*J. Pharm. Exp. Ther.* 288, pp. 1367-1373 (1999)). That is, compounds of the present invention were tested for their relaxant effects using the human urinary bladder detrusor in the constricted condition induced by carbachol ($0.5 \times 10^{-6}$ M). The fact that the urinary bladder detrusor was allowed to relax by the present compounds at $10^{-5}$ M suggests the effectiveness of the present compounds against urinary incontinence.

TEST EXAMPLE 5

Toxicity Test

Each of the present compounds synthesized in Examples 1 and 2 were orally administered to 6-week old male ddy mice (CHARLES RIVER JAPAN) at 100 mg/kg. The fact that none of the eight animals were found to be dead showed that these compounds have a low toxicity. The other compounds, which achieved the same results, were also shown to have a low toxicity.

All the publications, patents and patent applications cited in this specification are incorporated herein in their entities by reference.

INDUSTRIAL UTILITY

The compounds of the present invention are novel compounds. They are expected to compounds which are unlikely to induce any side effect due to drug interactions, since they have a high human β3-adrenoreceptor stimulating activity and a low drug metabolizing enzyme inhibiting activity. Therefore, compounds of the present invention are useful as medicines for treating and preventing β3-adrenoreceptor associated diseases including diabetes, obesity and hyperlipidemia. Compounds of the present invention are also useful as medicines for treating and preventing fatty liver, urinary incontinence and others.

The invention claimed is:

1. A compound of the formula

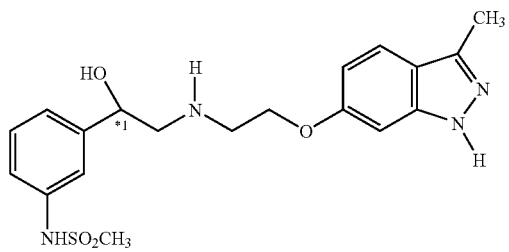

or a salt thereof.

2. The compound according to claim 1, in the form of a racemic mixture of optically active compounds, or a salt thereof.

3. A compound according to claim 1, in an isolated optically active form or a salt thereof.

4. A compound of the formula

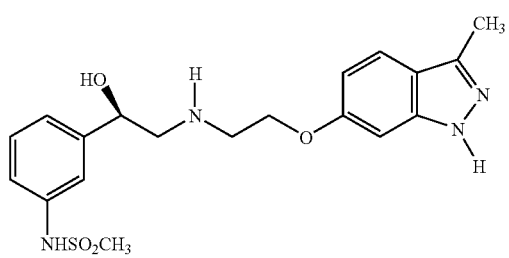

or a salt thereof.

5. A compound that undergoes in vivo metabolism to generate a compound according to claim 1.

6. A medicine comprising a compound according to claim 1 or a salt thereof as an active ingredient.

7. A medicine comprising a compound according to claim 2 or a salt thereof as an active ingredient.

8. A medicine comprising a compound according to claim 3 or a salt thereof as an active ingredient.

9. A medicine comprising a compound according to claim 4 or a salt thereof as an active ingredient.

10. A medicine comprising a compound according to claim 5 or a salt thereof as an active ingredient.

* * * * *